(12) United States Patent
Li

(10) Patent No.: US 8,026,412 B2
(45) Date of Patent: Sep. 27, 2011

(54) SOYBEAN MTH1 PROMOTER AND ITS USE IN CONSTITUTIVE EXPRESSION OF TRANSGENIC GENES IN PLANTS

(75) Inventor: Zhongsen Li, Hockessin, DE (US)

(73) Assignee: E. I. du Pont de Nemours and Company, Wilmington, DE (US)

(*) Notice: Subject to any disclaimer, the term of this patent is extended or adjusted under 35 U.S.C. 154(b) by 0 days.

(21) Appl. No.: 12/546,157

(22) Filed: Aug. 24, 2009

(65) Prior Publication Data

US 2010/0064390 A1    Mar. 11, 2010

Related U.S. Application Data

(60) Provisional application No. 61/095,333, filed on Sep. 9, 2008.

(51) Int. Cl.
*A01H 1/00* (2006.01)
*C07H 21/04* (2006.01)
*C12N 15/00* (2006.01)

(52) U.S. Cl. ........... 800/295; 435/6; 435/69.1; 435/468; 435/419; 435/320.1; 536/24.1; 800/278

(58) Field of Classification Search ............. 435/6, 69.1, 435/468, 419, 320.1; 536/24.1; 800/278, 800/295; 530/370
See application file for complete search history.

(56) References Cited

U.S. PATENT DOCUMENTS

2005/0155114 A1* 7/2005 Hinchey ....................... 800/288

FOREIGN PATENT DOCUMENTS

WO        0018963       4/2000

OTHER PUBLICATIONS

Hayakawa, Y. GenEmbl Database, Direct submission, Acc. No. AB243070, Nov. 29, 2008, Result 2.*
Ebert et al., Proc. Natl. Acad. Sci. USA. Identification of an Essential Upstream Element in the Nopaline Synthase Promoter by Stable and Transient Assays, vol. 84, p. 5745-5749, 1987.
Lawton et al., Plant Molecular Biology. Expression of a Soybean B-Conclycinin Gene Under the Control of the Cauliflower Mosaic Virus 35S and 19S Promoters in Transformed Petunia Tissues, vol. 9, p. 315-324, 1987.
Odell et al., Nature. Identification of DNA Sequences Required for Activity of the Cauliflower Mosaic Virus 35S Promoter, vol. 313, p. 810-812, 1985.
Sanger et al., Plant Molecular Biology. Characteristics of a Strong Promoter from Figwort Mosaic Virus: Comparison with the Analogous 35S Promoter from Cauliflower Mosaic Virus and the Regulated Mannopine Synthase Promoter, vol. 14, p. 433-443, 1990.
Kaegi et al., Biochemistry. Biochemistry of Metallothionein, vol. 27(23), p. 8509-8515, 1988.
Mueller et al., Genes & Development. Constitutive and Metal-Inducible Protein: DNA Interactions at the Mouse Metallothionein I Promoter Examined by in Vivo and in Vitro Footprinting, vol. 2(4), p. 412-427, 1988.
Bunch et al., Nucleic Acids Research. Characterization and Use of the Drosophila Metalloghionein Promoter in Cultured *Drosophila Melanogaster* Cells, vol. 16(3), p. 1043-1061, 1988.
Atanassova et al., Plant Molecular Biology. Functional Analysis of the Promoter Region of a Maize (*Zea mays* L.) H3 Histone Gene in Transgenic *Arabidopsis thaliana*, vol. 37, p. 275-285, 1998.
Battraw et al., Plant Molecular Biology. Histochemical Analysis of CaMV 35S Promoter-B-Glucuronidase Gene Expression in Transgenic Rice Plants, vol. 15, p. 527-538, 1990.
Holtorf et al., Plant Molecular Biology. Comparison of Different Constitutive and Inducible Promoters for the Overexpression of Transgenes in *Arabidopsis thaliana*, vol. 29, p. 637-646, 1995.
Jefferson et al., The EMBO Journal. GUS fusions: B-Glucuronidase as a Sensitive and Versatile Gene Fusion Marker in Higher Plants, vol. 6, p. 3901-3907, 1987.
Wilmink et al., Plant Molecular Biology. Activity of Constitutive Promoters in Various Species from the *Liliaceae*, vol. 29, p. 949-955, 1995.
Plant et al., Plant Molecular Biology. Regulation of an *Arabidopsis oleosin* Gene Promoter in Transgenic *Brassica Napus*, vol. 25, p. 193-205, 1994.
Zhongsen Li, Texas A&M University Ph.D. dissertation. Isolation and Characterization of *Arabidopsis* Embryo-Specific Genes, p. 107-128, 1997.
Callis et al., Journal of Biological Chemistry. Ubiquitin Extension Proteins of *Arabidopsis thaliana*, vol. 265(21), p. 12486-12493, 1990.
Rollfinke et al., Gene. Characterization and Expression of a Heptaubiquitin Gene from Tomato, vol. 211, p. 267-276, 1998.
National Center for Biotechnology Information, General Identifier No. 47076853, Accession No. AB176559, May 7, 2004, Sun et al., Metallothionein cDNAs from Leguminous Plants.
National Center for Biotechnology Information, General Identifier No. 47076854, Accession No. BAD18377, May 7, 2004, Sun et al., Metallothionein cDNAs from Leguminous Plants.

* cited by examiner

*Primary Examiner* — Phuong T Bui

(57) ABSTRACT

The promoter of a soybean metallothionein protein (MTH1) and fragments thereof and their use in promoting the expression of one or more heterologous nucleic acid fragments in a tissue-independent or constitutive manner in plants are described.

14 Claims, 9 Drawing Sheets

(2 of 9 Drawing Sheet(s) Filed in Color)

SOYBEAN MTH1 PROMOTER AND ITS USE IN CONSTITUTIVE EXPRESSION OF TRANSGENIC GENES IN PLANTS

This application claims the benefit of U.S. Provisional Application No. 61/095,333, filed Sep. 9, 2008, the entire content of which is herein incorporated by reference.

FIELD OF THE INVENTION

This invention relates to a plant promoter GM-MTH1 and fragments thereof and their use in altering expression of at least one heterologous nucleic acid fragment in plants in a tissue-independent or constitutive manner.

BACKGROUND OF THE INVENTION

Recent advances in plant genetic engineering have opened new doors to engineer plants to have improved characteristics or traits, such as plant disease resistance, insect resistance, herbicidal resistance, yield improvement, improvement of the nutritional quality of the edible portions of the plant, and enhanced stability or shelf-life of the ultimate consumer product obtained from the plants. Thus, a desired gene (or genes) with the molecular function to impart different or improved characteristics or qualities, can be incorporated properly into the plant's genome. The newly integrated gene (or genes) coding sequence can then be expressed in the plant cell to exhibit the desired new trait or characteristics. It is important that appropriate regulatory signals must be present in proper configurations in order to obtain the expression of the newly inserted gene coding sequence in the plant cell. These regulatory signals typically include a promoter region, a 5' non-translated leader sequence and a 3' transcription termination/polyadenylation sequence.

A promoter is a non-coding genomic DNA sequence, usually upstream (5') to the relevant coding sequence, to which RNA polymerase binds before initiating transcription. This binding aligns the RNA polymerase so that transcription will initiate at a specific transcription initiation site. The nucleotide sequence of the promoter determines the nature of the enzyme and other related protein factors that attach to it and the rate of RNA synthesis. The RNA is processed to produce messenger RNA (mRNA) which serves as a template for translation of the RNA sequence into the amino acid sequence of the encoded polypeptide. The 5' non-translated leader sequence is a region of the mRNA upstream of the coding region that may play a role in initiation and translation of the mRNA. The 3' transcription termination/polyadenylation signal is a non-translated region downstream of the coding region that functions in the plant cell to cause termination of the RNA synthesis and the addition of polyadenylate nucleotides to the 3' end.

It has been shown that certain promoters are able to direct RNA synthesis at a higher rate than others. These are called "strong promoters". Certain other promoters have been shown to direct RNA synthesis at higher levels only in particular types of cells or tissues and are often referred to as "tissue specific promoters", or "tissue-preferred promoters" if the promoters direct RNA synthesis preferably in certain tissues but also in other tissues at reduced levels. Since the patterns of the expression of a chimeric gene (or genes) introduced into a plant are controlled using promoters, there is an ongoing interest in the isolation of novel promoters which are capable of controlling the expression of a chimeric gene or (genes) at certain levels in specific tissue types or at specific plant developmental stages.

Certain promoters are able to direct RNA synthesis at relatively similar levels across all tissues of a plant. These are called "constitutive promoters" or "tissue—independent" promoters. Constitutive promoters can be divided into strong, moderate and weak according to their effectiveness to direct RNA synthesis. Since it is necessary in many cases to simultaneously express a chimeric gene (or genes) in different tissues of a plant to get the desired functions of the gene (or genes), constitutive promoters are especially useful in this consideration. Though many constitutive promoters have been discovered from plants and plant viruses and characterized, there is still an ongoing interest in the isolation of more novel constitutive promoters which are capable of controlling the expression of a chimeric gene or (genes) at different levels and the expression of multiple genes in the same transgenic plant for gene stacking.

SUMMARY OF THE INVENTION

This invention concerns an isolated nucleic acid fragment comprising a promoter wherein said promoter consists essentially of the nucleotide sequence set forth in SEQ ID NOs: 1, 2, 3, 4, 5, 6 or said promoter consists essentially of a fragment that is substantially similar and functionally equivalent to the nucleotide sequence set forth in SEQ ID NOs: 1, 2, 3, 4, 5, 6.

In a second embodiment, this invention concerns a recombinant expression construct comprising at least one heterologous nucleic acid fragment operably linked to the promoter of the invention.

In a third embodiment, this invention concerns a cell, plant, or seed comprising a recombinant expression construct of the present disclosure.

In a fourth embodiment, this invention concerns plants comprising this recombinant expression construct and seeds obtained from such plants.

In a fifth embodiment, this invention concerns a method of altering (increasing or decreasing) expression of at least one heterologous nucleic acid fragment in a plant cell which comprises:
  (a) transforming a plant cell with the recombinant expression construct described above;
  (b) growing fertile mature plants from the transformed plant cell of step (a);
  (c) selecting plants containing the transformed plant cell wherein the expression of the heterologous nucleic acid fragment is increased or decreased.

In a sixth embodiment, this invention concerns a method for expressing a yellow fluorescent protein ZS-YELLOW1 N1 in a host cell comprising:
  (a) transforming a host cell with a recombinant expression construct comprising at least one ZS-YELLOW1 N1 (YFP) nucleic acid fragment operably linked to a promoter wherein said promoter consists essentially of the nucleotide sequence set forth in SEQ ID NOs:1, 2, 3, 4, 5, or 6; and
  (b) growing the transformed host cell under conditions that are suitable for expression of the recombinant DNA construct, wherein expression of the recombinant DNA construct results in production of increased levels of ZS-YELLOW1 N1 protein in the transformed host cell when compared to a corresponding nontransformed host cell.

In a seventh embodiment, this invention concerns an isolated nucleic acid fragment comprising a plant metallothionein protein (MTH1) gene promoter.

In an eighth embodiment, this invention concerns a method of altering a marketable plant trait. The marketable plant trait concerns genes and proteins involved in disease resistance, herbicide resistance, insect resistance, carbohydrate metabolism, fatty acid metabolism, amino acid metabolism, plant development, plant growth regulation, yield improvement, drought resistance, cold resistance, heat resistance, and salt resistance.

In a ninth embodiment, this invention concerns an isolated polynucleotide linked to a heterologous nucleic acid sequence. The heterologous nucleic acid sequence encodes a protein involved in disease resistance, herbicide resistance, insect resistance; carbohydrate metabolism, fatty acid metabolism, amino acid metabolism, plant development, plant growth regulation, yield improvement, drought resistance, cold resistance, heat resistance, or salt resistance in plants.

BRIEF DESCRIPTION OF THE DRAWINGS AND SEQUENCE LISTINGS

The patent or application file contains at least one drawing executed in color. Copies of this patent or patent application publication with color drawing(s) will be provided by the Office upon request and payment of the necessary fee.

The invention can be more fully understood from the following detailed description and the accompanying drawings and Sequence Listing that form a part of this application.

Figure 1:
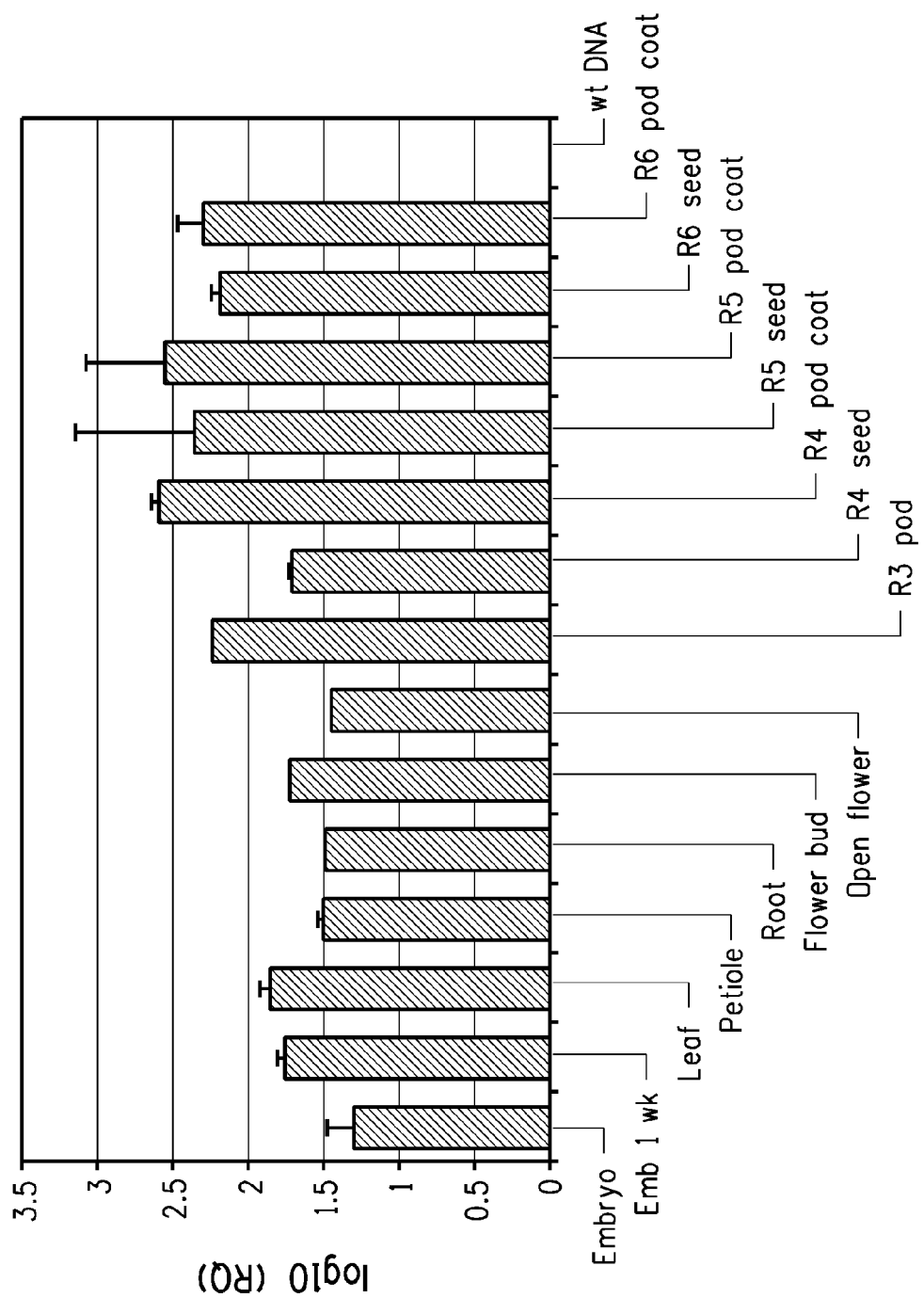
FIG. 1 is the logarithm of relative quantifications of the soybean MTH1 gene expression in 14 different soybean tissues by quantitative RT-PCR. The gene expression profile indicates that the MTH1 gene is highly expressed in all the checked tissues.

The patent or application file contains at least one drawing executed in color. Copies of this patent or patent application publication with color drawing(s) will be provided by the Office upon request and payment of the necessary fee.

The sequence descriptions summarize the Sequence Listing attached hereto. The Sequence Listing contains one letter codes for nucleotide sequence characters and the single and three letter codes for amino acids as defined in the IUPAC-IUB standards described in *Nucleic Acids Research* 13:3021-3030 (1985) and in the *Biochemical Journal* 219 (2):345-373 (1984).

A Sequence Listing is provided herewith on Compact Disk. The contents of the Compact Disk containing the Sequence Listing are hereby incorporated by reference in compliance with 37 C.F.R. §1.52(e).

SEQ ID NO:1 is the DNA sequence comprising a 1658 bp (base pair) soybean MTH1 promoter.

SEQ ID NO:2 is a 1255 bp truncated form of the MTH1 promoter shown in SEQ ID NO:1 (bp 404-1658 of SEQ ID NO:1).

SEQ ID NO:3 is a 1003 bp truncated form of the MTH1 promoter shown in SEQ ID NO:1 (bp 656-1658 of SEQ ID NO:1).

SEQ ID NO:4 is a 775 bp truncated form of the MTH1 promoter shown in SEQ ID NO:1 (bp 884-1658 of SEQ ID NO:1).

SEQ ID NO:5 is a 513 bp truncated form of the MTH1 promoter shown in SEQ ID NO:1 (bp 1146-1658 of SEQ ID NO:1).

SEQ ID NO:6 is a 262 bp truncated form of the MTH1 promoter shown in SEQ ID NO:1 (bp 1397-1658 of SEQ ID NO:1).

SEQ ID NO:7 is an oligonucleotide primer used as a sense primer in the PCR amplification of the full length MTH1 promoter in SEQ ID NO:1 when paired with SEQ ID NO:8. A restriction enzyme XmaI recognition site CCCGGG is included for subsequent cloning.

SEQ ID NO:8 is an oligonucleotide primer used as an antisense primer in the PCR amplification of the full length MTH1 promoter in SEQ ID NO:1 when paired with SEQ ID NO:7. A restriction enzyme NcoI recognition site CCATGG is included for subsequent cloning.

SEQ ID NO:9 is an oligonucleotide primer used as an antisense primer in the PCR amplifications of the truncated MTH1 promoters in SEQ ID NOs:2, 3, 4, 5, or 6 when paired with SEQ ID NOs:10, 11, 12, 13, or 14, respectively.

SEQ ID NO:10 is an oligonucleotide primer used as a sense primer in the PCR amplification of the truncated MTH1 promoter in SEQ ID NO:2 when paired with SEQ ID NO:9.

SEQ ID NO:11 is an oligonucleotide primer used as a sense primer in the PCR amplification of the truncated MTH1 promoter in SEQ ID NO:3 when paired with SEQ ID NO:9.

SEQ ID NO:12 is an oligonucleotide primer used as a sense primer in the PCR amplification of the truncated MTH1 promoter in SEQ ID NO:4 when paired with SEQ ID NO:9.

SEQ ID NO:13 is an oligonucleotide primer used as a sense primer in the PCR amplification of the truncated MTH1 promoter in SEQ ID NO:5 when paired with SEQ ID NO:9.

SEQ ID NO:14 is an oligonucleotide primer used as a sense primer in the PCR amplification of the truncated MTH1 promoter in SEQ ID NO:6 when paired with SEQ ID NO:9.

SEQ ID NO:15 is the 574 bp nucleotide sequence of the putative soybean metallothionein protein gene MTH1 (PSO333209). Nucleotides 1 to 78 are the 5' untranslated sequence, nucleotides 79 to 81 are the translation initiation codon, nucleotides 79 to 315 are the polypeptide coding region, nucleotides 316 to 318 are the termination codon, and nucleotides 319 to 574 are part of the 3' untranslated sequence.

SEQ ID NO:16 is the predicted 79 aa (amino acid) long peptide sequence translated from the coding region of the putative soybean metallothionein protein gene MTH1 nucleotide sequence SEQ ID NO:15.

SEQ ID NO:17 is the 4942 bp sequence of QC371.

SEQ ID NO:18 is the 9467 bp sequence of QC383.

SEQ ID NO:19 is the 4913 bp sequence of QC371-1Y.

SEQ ID NO:20 is an oligonucleotide primer used in the diagnostic PCR to check for soybean genomic DNA presence in total RNA or cDNA when paired with SEQ ID NO:21.

SEQ ID NO:21 is an oligonucleotide primer used in the diagnostic PCR to check for soybean genomic DNA presence in total RNA or cDNA when paired with SEQ ID NO:20.

SEQ ID NO:22 is a sense primer used in quantitative RT-PCR analysis of PSO333209 gene expression.

SEQ ID NO:23 is an antisense primer used in quantitative RT-PCR analysis of PSO333209 gene expression.

SEQ ID NO:24 is a sense primer used as an endogenous control gene primer in quantitative RT-PCR analysis of gene expression.

SEQ ID NO:25 is an antisense primer used as an endogenous control gene primer in quantitative RT-PCR analysis of gene expression.

SEQ ID NO:26 is a PSO333209 gene-specific sense primer used together with SEQ ID NO:27 to screen BAC (bacterial artificial chromosome) libraries to identify corresponding BAC clones.

SEQ ID NO:27 is a PSO333209 gene-specific antisense primer used together with SEQ ID NO:26 to screen BAC libraries to identify corresponding BAC clones.

SEQ ID NO:28 is a sense primer used in quantitative PCR analysis of SAMS:ALS transgene copy numbers.

SEQ ID NO:29 is a FAM labeled fluorescent DNA oligo probe used in quantitative PCR analysis of SAMS:ALS transgene copy numbers.

SEQ ID NO:30 is an antisense primer used in quantitative PCR analysis of SAMS:ALS transgene copy numbers.

SEQ ID NO:31 is a sense primer used in quantitative PCR analysis of GM-MTH1:YFP transgene copy numbers.

SEQ ID NO:32 is a FAM labeled fluorescent DNA oligo probe used in quantitative PCR analysis of GM-MTH1:YFP transgene copy numbers.

SEQ ID NO:33 is an antisense primer used in quantitative PCR analysis of GM-MTH1:YFP transgene copy numbers.

SEQ ID NO:34 is a sense primer used as an endogenous control gene primer in quantitative PCR analysis of transgene copy numbers.

SEQ ID NO:35 is a VIC labeled DNA oligo probe used as an endogenous control gene probe in quantitative PCR analysis of transgene copy numbers.

SEQ ID NO:36 is an antisense primer used as an endogenous control gene primer in quantitative PCR analysis of transgene copy numbers.

SEQ ID NO:37 is the recombination site attL1 sequence in the GATEWAY® cloning system (Invitrogen, Carlsbad, Calif.).

SEQ ID NO:38 is the recombination site attL2 sequence in the GATEWAY® cloning system (Invitrogen).

SEQ ID NO:39 is the recombination site attR1 sequence in the GATEWAY® cloning system (Invitrogen).

SEQ ID NO:40 is the recombination site attR2 sequence in the GATEWAY® cloning system (Invitrogen).

SEQ ID NO:41 is the recombination site attB1 sequence in the GATEWAY® cloning system (Invitrogen).

SEQ ID NO:42 is the recombination site attB2 sequence in the GATEWAY® cloning system (Invitrogen).

SEQ ID NO:43 is the 8409 bp sequence of QC324i used as a destination vector in GATEWAY® cloning.

SEQ ID NO:44 is the 5286 bp sequence of QC330 used as a destination vector in GATEWAY® cloning.

SEQ ID NO:45 is the nucleotide sequence of the *Glycine max* type 2 metallothionein (NCBI Accession No. AB176559 (GI47076853, locus AB176559)

SEQ ID NO:46 is the amino acid sequence of the *Glycine max* type 2 metallothionein (NCBI Accession No. BAD18377.1 (GI:47076854, locus BAS18377).

DETAILED DESCRIPTION OF THE INVENTION

The disclosure of all patents, patent applications, and publications cited herein are incorporated by reference in their entirety.

In the context of this disclosure, a number of terms shall be utilized.

As used herein, a "GM-MTH1 promoter" refers to the promoter of a putative *Glycine max* gene with significant homology to type II metallothionein genes identified in various plant species including soybean that are deposited in National Center for Biotechnology Information (NCBI) database.

The term "constitutive promoter" refers to promoters active in all or most tissues of a plant at all or most developing stages. As with other promoters classified as "constitutive" (e.g. ubiquitin), some variation in absolute levels of expression can exist among different tissues or stages.

The term "constitutive promoter" or "tissue-independent" are used interchangeably herein.

The promoter nucleotide sequences and methods disclosed herein are useful in regulating constitutive expression of any heterologous nucleotide sequences in a host plant in order to alter the phenotype of a plant.

Various changes in phenotype are of interest including, but not limited to, modifying the fatty acid composition in a plant, altering the amino acid content of a plant, altering a plant's pathogen defense mechanism, and the like. These results can be achieved by providing expression of heterologous products or increased expression of endogenous products in plants. Alternatively, the results can be achieved by providing for a reduction of expression of one or more endogenous products, particularly enzymes or cofactors in the plant. These changes result in a change in phenotype of the transformed plant.

Genes of interest are reflective of the commercial markets and interests of those involved in the development of the crop. Crops and markets of interest change, and as developing nations open up world markets, new crops and technologies will emerge also. In addition, as our understanding of agronomic characteristics and traits such as yield and heterosis increase, the choice of genes for transformation will change accordingly. General categories of genes of interest include, but are not limited to, those genes involved in information, such as zinc fingers, those involved in communication, such as kinases, and those involved in housekeeping, such as heat shock proteins. More specific categories of transgenes, for example, include, but are not limited to, genes encoding important traits for agronomics, insect resistance, disease resistance, herbicide resistance, sterility, grain or seed characteristics, and commercial products. Genes of interest include, generally, those involved in oil, starch, carbohydrate, or nutrient metabolism as well as those affecting seed size, plant development, plant growth regulation, and yield improvement. Plant development and growth regulation also refer to the development and growth regulation of various parts of a plant, such as the flower, seed, root, leaf and shoot.

Other commercially desirable traits are genes and proteins conferring cold, heat, salt, and drought resistance.

Disease and/or insect resistance genes may encode resistance to pests that have great yield drag such as for example, anthracnose, soybean mosaic virus, soybean cyst nematode, root-knot nematode, brown leaf spot, Downy mildew, purple seed stain, seed decay and seedling diseases caused commonly by the fungi—*Pythium* sp., *Phytophthora* sp., *Rhizoctonia* sp., *Diaporthe* sp. Bacterial blight caused by the bacterium *Pseudomonas syringae* pv. *Glycinea*. Genes conferring insect resistance include, for example, *Bacillus thuringiensis* toxic protein genes (U.S. Pat. Nos. 5,366,892; 5,747,450; 5,737,514; 5,723,756; 5,593,881; and Geiser et al (1986) Gene 48:109); lectins (Van Damme et al. (1994) Plant Mol. Biol. 24:825); and the like.

Herbicide resistance traits may include genes coding for resistance to herbicides that act to inhibit the action of acetolactate synthase (ALS), in particular the sulfonylurea-type herbicides (e.g., the acetolactate synthase ALS gene containing mutations leading to such resistance, in particular the S4 and/or HRA mutations). The ALS-gene mutants encode resistance to the herbicide chlorsulfuron. Glyphosate acetyl transferase (GAT) is an N-acetyltransferase from *Bacillus licheniformis* that was optimized by gene shuffling for acetylation of the broad spectrum herbicide, glyphosate, forming the basis of a novel mechanism of glyphosate tolerance in transgenic plants (Castle et al. (2004) *Science* 304, 1151-1154).

Antibiotic resistance genes include, for example, neomycin phosphotransferase (npt) and hygromycin phosphotransferase (hpt). Two neomycin phosphotransferase genes are used in selection of transformed organisms: the neomycin phosphotransferase I (nptI) gene and the neomycin phosphotransferase II (nptII) gene. The second one is more widely used. It was initially isolated from the transposon Tn5 that was present in the bacterium strain *Escherichia coli* K12. The gene codes for the aminoglycoside 3'-phosphotransferase (denoted aph(3')-II or NPTII) enzyme, which inactivates by phosphorylation a range of aminoglycoside antibiotics such as kanamycin, neomycin, geneticin and paroromycin. NPTII is widely used as a selectable marker for plant transformation. It is also used in gene expression and regulation studies in different organisms in part because N-terminal fusions can be constructed that retain enzyme activity. NPTII protein activity can be detected by enzymatic assay. In other detection methods, the modified substrates, the phosphorylated antibiotics, are detected by thin-layer chromatography, dot-blot analysis or polyacrylamide gel electrophoresis. Plants such as maize, cotton, tobacco, *Arabidopsis*, flax, soybean and many others have been successfully transformed with the nptII gene.

The hygromycin phosphotransferase (denoted hpt, hph or aphIV) gene was originally derived from *Escherichia coli*. The gene codes for hygromycin phosphotransferase (HPT), which detoxifies the aminocyclitol antibiotic hygromycin B. A large number of plants have been transformed with the hpt gene and hygromycin B has proved very effective in the selection of a wide range of plants, including monocotyledonous. Most plants exhibit higher sensitivity to hygromycin B than to kanamycin, for instance cereals. Likewise, the hpt gene is used widely in selection of transformed mammalian cells. The sequence of the hpt gene has been modified for its use in plant transformation. Deletions and substitutions of amino acid residues close to the carboxy (C)-terminus of the enzyme have increased the level of resistance in certain plants, such as tobacco. At the same time, the hydrophilic C-terminus of the enzyme has been maintained and may be essential for the strong activity of HPT. HPT activity can be checked using an enzymatic assay. A non-destructive callus induction test can be used to verify hygromycin resistance.

Genes involved in plant growth and development have been identified in plants. One such gene, which is involved in cytokinin biosynthesis, is isopentenyl transferase (IPT). Cytokinin plays a critical role in plant growth and development by stimulating cell division and cell differentiation (Sun et al. (2003), Plant Physiol. 131: 167-176).

Calcium-dependent protein kinases (CDPK), a family of serine-threonine kinase found primarily in the plant kingdom, are likely to function as sensor molecules in calcium-mediated signaling pathways. Calcium ions are important second messengers during plant growth and development (Harper et al. Science 252, 951-954 (1993); Roberts et al. Curr Opin Cell Biol 5, 242-246 (1993); Roberts et al. Annu Rev Plant Mol Biol 43, 375-414 (1992)).

Nematode responsive protein (NRP) is produced by soybean upon the infection of soybean cyst nematode. NRP has homology to a taste-modifying glycoprotein miraculin and the NF34 protein involved in tumor formation and hyper response induction. NRP is believed to function as a defense-inducer in response to nematode infection (Tenhaken et al. BMC Bioinformatics 6:169 (2005)).

The quality of seeds and grains is reflected in traits such as levels and types of fatty acids or oils, saturated and unsaturated, quality and quantity of essential amino acids, and levels of carbohydrates. Therefore, commercial traits can also be encoded on a gene or genes that could increase for example methionine and cysteine, two sulfur containing amino acids that are present in low amounts in soybeans. Cystathionine gamma synthase (CGS) and serine acetyl transferase (SAT) are proteins involved in the synthesis of methionine and cysteine, respectively.

Other commercial traits can encode genes to increase for example monounsaturated fatty acids, such as oleic acid, in oil seeds. Soybean oil for example contains high levels of polyunsaturated fatty acids and is more prone to oxidation than oils with higher levels of monounsaturated and saturated fatty acids. High oleic soybean seeds can be prepared by recombinant manipulation of the activity of oleoyl 12-desaturase (Fad2). High oleic soybean oil can be used in applications that require a high degree of oxidative stability, such as cooking for a long period of time at an elevated temperature.

Raffinose saccharides accumulate in significant quantities in the edible portion of many economically significant crop species, such as soybean (*Glycine max* L. Merrill), sugar beet (*Beta vulgaris*), cotton (*Gossypium hirsutum* L.), canola (*Brassica* sp.) and all of the major edible leguminous crops including beans (*Phaseolus* sp.), chick pea (*Cicer arietinum*), cowpea (*Vigna unguiculata*), mung bean (*Vigna radiata*), peas (*Pisum sativum*), lentil (*Lens culinaris*) and lupine (*Lupinus* sp.). Although abundant in many species, raffinose saccharides are an obstacle to the efficient utilization of some economically important crop species.

Down regulation of the expression of the enzymes involved in raffinose saccharide synthesis, such as galactinol synthase for example, would be a desirable trait.

In certain embodiments, the present invention contemplates the transformation of a recipient cell with more than one advantageous transgene. Two or more transgenes can be supplied in a single transformation event using either distinct transgene-encoding vectors, or a single vector incorporating two or more gene coding sequences. Any two or more transgenes of any description, such as those conferring herbicide, insect, disease (viral, bacterial, fungal, and nematode) or drought resistance, oil quantity and quality, or those increasing yield or nutritional quality may be employed as desired.

An "isolated nucleic acid fragment" refers to a polymer of ribonucleotides (RNA) or deoxyribonucleotides (DNA) that is single- or double-stranded, optionally containing synthetic, non-natural or altered nucleotide bases. An isolated nucleic acid fragment in the form of DNA may be comprised of one or more segments of cDNA, genomic DNA or synthetic DNA.

The terms "polynucleotide", "polynucleotide sequence", "nucleic acid sequence", and "nucleic acid fragment"/"isolated nucleic acid fragment" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. Nucleotides (usually found in their 5'-monophosphate form) are referred to by a single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

A "heterologous nucleic acid fragment" refers to a sequence that is not naturally occurring with the plant promoter sequence of the invention. While this nucleotide sequence is heterologous to the promoter sequence, it may be homologous, or native, or heterologous, or foreign, to the plant host. However, it is recognized that the instant promoters may be used with their native coding sequences to increase or decrease expression resulting in a change in phenotype in the transformed seed.

The terms "subfragment that is functionally equivalent" and "functionally equivalent subfragment" are used interchangeably herein. These terms refer to a portion or subsequence of an isolated nucleic acid fragment in which the ability to alter gene expression or produce a certain phenotype is retained whether or not the fragment or subfragment encodes an active enzyme. For example, the fragment or subfragment can be used in the design of chimeric genes to produce the desired phenotype in a transformed plant. Chimeric genes can be designed for use in co-suppression or antisense by linking a nucleic acid fragment or subfragment thereof, whether or not it encodes an active enzyme, in the appropriate orientation relative to a plant promoter sequence.

The terms "substantially similar" and "corresponding substantially" as used herein refer to nucleic acid fragments wherein changes in one or more nucleotide bases do not affect the ability of the nucleic acid fragment to mediate gene expression or produce a certain phenotype. These terms also refer to modifications of the nucleic acid fragments of the instant invention such as deletion or insertion of one or more nucleotides that do not substantially alter the functional properties of the resulting nucleic acid fragment relative to the initial, unmodified fragment. It is therefore understood, as those skilled in the art will appreciate, that the invention encompasses more than the specific exemplary sequences.

The isolated promoter sequence of the present invention can be modified to provide a range of constitutive expression levels of the heterologous nucleotide sequence. Thus, less than the entire promoter regions may be utilized and the ability to drive expression of the coding sequence retained. However, it is recognized that expression levels of the mRNA may be decreased with deletions of portions of the promoter sequences. Likewise, the tissue-independent, constitutive nature of expression may be changed.

Modifications of the isolated promoter sequences of the present invention can provide for a range of constitutive expression of the heterologous nucleotide sequence. Thus, they may be modified to be weak constitutive promoters or strong constitutive promoters. Generally, by "weak promoter" is intended a promoter that drives expression of a coding sequence at a low level. By "low level" is intended at levels about 1/10,000 transcripts to about 1/100,000 transcripts to about 1/500,000 transcripts. Conversely, a strong promoter drives expression of a coding sequence at high level, or at about 1/10 transcripts to about 1/100 transcripts to about 1/1,000 transcripts.

Nucleic acid molecules that are fragments of the promoter of the present invention comprise at least 20, 50, 75, 100, 150, 200, 250, 300, 350, 400, 450, 500 nucleotides, or up to the number of nucleotides present in a full-length nucleotide sequence disclosed herein (for example 1658, SEQ ID NO:1).

Moreover, the skilled artisan recognizes that substantially similar nucleic acid sequences encompassed by this invention are also defined by their ability to hybridize, under moderately stringent conditions (for example, 0.5×SSC, 0.1% SDS, 60° C.) with the sequences exemplified herein, or to any portion of the nucleotide sequences reported herein and which are functionally equivalent to the promoter of the invention. Estimates of such homology are provided by either DNA-DNA or DNA-RNA hybridization under conditions of stringency as is well understood by those skilled in the art (Hames and Higgins, Eds.; In Nucleic Acid Hybridisation; IRL Press: Oxford, U.K., 1985). Stringency conditions can be adjusted to screen for moderately similar fragments, such as homologous sequences from distantly related organisms, to highly similar fragments, such as genes that duplicate functional enzymes from closely related organisms. Post-hybridization washes partially determine stringency conditions. One set of conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. Another set of stringent conditions uses higher temperatures in which the washes are identical to those above except for the temperature of the final two 30 min washes in 0.2× SSC, 0.5% SDS was increased to 60° C. Another set of highly stringent conditions uses two final washes in 0.1×SSC, 0.1% SDS at 65° C.

Preferred substantially similar nucleic acid sequences encompassed by this invention are those sequences that are 80% identical to the nucleic acid fragments reported herein or which are 80% identical to any portion of the nucleotide sequences reported herein. More preferred are nucleic acid fragments which are 90% identical to the nucleic acid sequences reported herein, or which are 90% identical to any portion of the nucleotide sequences reported herein. Most preferred are nucleic acid fragments which are 95% identical to the nucleic acid sequences reported herein, or which are 95% identical to any portion of the nucleotide sequences reported herein. It is well understood by one skilled in the art that many levels of sequence identity are useful in identifying related polynucleotide sequences. Useful examples of percent identities are those listed above, or also preferred is any integer percentage from 80% to 100%, such as 81%, 82%, 83%, 84%, 85%, 86%, 87%, 88%, 89%, 90%, 91%, 92%, 93%, 94%, 95%, 96%, 97%, 98 and 99%.

A "substantially homologous sequence" refers to variants of the disclosed sequences such as those that result from site-directed mutagenesis, as well as synthetically derived sequences. A substantially homologous sequence of the present invention also refers to those fragments of a particular promoter nucleotide sequence disclosed herein that operate to promote the constitutive expression of an operably linked heterologous nucleic acid fragment. These promoter fragments will comprise at least about 20 contiguous nucleotides, preferably at least about 50 contiguous nucleotides, more preferably at least about 75 contiguous nucleotides, even more preferably at least about 100 contiguous nucleotides of the particular promoter nucleotide sequence disclosed herein. The nucleotides of such fragments will usually comprise the TATA recognition sequence of the particular promoter sequence. Such fragments may be obtained by use of restriction enzymes to cleave the naturally occurring promoter nucleotide sequences disclosed herein; by synthesizing a nucleotide sequence from the naturally occurring promoter DNA sequence; or may be obtained through the use of PCR technology. See particularly, Mullis et al., Methods Enzymol. 155:335-350 (1987), and Higuchi, R. In PCR Technology: Principles and Applications for DNA Amplifications; Erlich, H. A., Ed.; Stockton Press Inc.: New York, 1989. Again, variants of these promoter fragments, such as those resulting from site-directed mutagenesis, are encompassed by the compositions of the present invention.

"Codon degeneracy" refers to divergence in the genetic code permitting variation of the nucleotide sequence without affecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

Sequence alignments and percent similarity calculations may be determined using the Megalign program of the LASARGENE bioinformatics computing suite (DNASTAR Inc., Madison, Wis.) or using the AlignX program of the Vector NTI bioinformatics computing suite (Invitrogen). Multiple alignment of the sequences are performed using the Clustal method of alignment (Higgins and Sharp, CABIOS 5:151-153 (1989)) with the default parameters (GAP PENALTY=10, GAP LENGTH PENALTY=10). Default parameters for pairwise alignments and calculation of percent identity of protein sequences using the Clustal method are KTUPLE=1, GAP PENALTY=3, WINDOW=5 and DIAGONALS SAVED=5. For nucleic acids these parameters are GAP PENALTY=10, GAP LENGTH PENALTY=10, KTUPLE=2, GAP PENALTY=5, WINDOW=4 and DIAGONALS SAVED=4. A "substantial portion" of an amino acid or nucleotide sequence comprises enough of the amino acid sequence of a polypeptide or the nucleotide sequence of a gene to afford putative identification of that polypeptide or gene, either by manual evaluation of the sequence by one skilled in the art, or by computer-automated sequence comparison and identification using algorithms such as BLAST (Altschul, S. F. et al., J. Mol. Biol. 215:403-410 (1993)) and Gapped Blast (Altschul, S. F. et al., Nucleic Acids Res. 25:3389-3402 (1997)). BLASTN refers to a BLAST program that compares a nucleotide query sequence against a nucleotide sequence database.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" or "recombinant expression construct", which are used interchangeably, refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a DNA sequence which codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to, promoters, translation leader sequences, introns, and polyadenylation recognition sequences.

"Promoter" refers to a DNA sequence capable of controlling the expression of a coding sequence or functional RNA. Functional RNA includes, but is not limited to, transfer RNA (tRNA) and ribosomal RNA (rRNA). The promoter sequence consists of proximal and more distal upstream elements, the latter elements often referred to as enhancers. Accordingly, an "enhancer" is a DNA sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters which cause a gene to be expressed in most cell types at most times are commonly referred to as "constitutive promoters". New promoters of various types useful in plant cells are constantly being discovered; numerous examples may be found in the compilation by Okamuro and Goldberg (Biochemistry of Plants 15:1-82 (1989)). It is further recognized that since in most cases the exact boundaries of regulatory sequences have not been completely defined, DNA fragments of some variation may have identical promoter activity. An "intron" is an intervening sequence in a gene that is transcribed into RNA but is then excised in the process of generating the mature mRNA. The term is also used for the excised RNA sequences. An "exon" is a portion of the sequence of a gene that is transcribed and is found in the mature messenger RNA derived from the gene, but is not necessarily a part of the sequence that encodes the final gene product.

Among the most commonly used promoters are the nopaline synthase (NOS) promoter (Ebert et al., Proc. Natl. Acad. Sci. U.S.A. 84:5745-5749 (1987)), the octapine synthase (OCS) promoter, caulimovirus promoters such as the cauliflower mosaic virus (CaMV) 19S promoter (Lawton et al., Plant Mol. Biol. 9:315-324 (1987)), the CaMV 35S promoter (Odell et al., Nature 313:810-812 (1985)), and the figwort mosaic virus 35S promoter (Sanger et al., Plant Mol. Biol. 14:433-43 (1990)), the light inducible promoter from the small subunit of rubisco, the Adh promoter (Walker et al., Proc. Natl. Acad. Sci. U.S.A. 84:6624-66280 (1987), the sucrose synthase promoter (Yang et al., Proc. Natl. Acad. Sci. U.S.A. 87:4144-4148 (1990)), the R gene complex promoter (Chandler et al., Plant Cell 1:1175-1183 (1989)), the chlorophyll a/b binding protein gene promoter, etc. Other commonly used promoters are, the promoters for the potato tuber ADPGPP genes, the sucrose synthase promoter, the granule bound starch synthase promoter, the glutelin gene promoter, the maize waxy promoter, Brittle gene promoter, and Shrunken 2 promoter, the acid chitinase gene promoter, and the zein gene promoters (15 kD, 16 kD, 19 kD, 22 kD, and 27 kD; Perdersen et al., Cell 29:1015-1026 (1982)). A plethora of promoters is described in PCT Publication No. WO 00/18963 published on Apr. 6, 2000, the disclosure of which is hereby incorporated by reference.

The "translation leader sequence" refers to a DNA sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner, R. and Foster, G. D., Molecular Biotechnology 3:225 (1995)).

The "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al., Plant Cell 1:671-680 (1989).

"RNA transcript" refers to a product resulting from RNA polymerase-catalyzed transcription of a DNA sequence. When an RNA transcript is a perfect complementary copy of a DNA sequence, it is referred to as a primary transcript or it may be a RNA sequence derived from posttranscriptional processing of a primary transcript and is referred to as a mature RNA. "Messenger RNA" ("mRNA") refers to RNA that is without introns and that can be translated into protein by the cell. "cDNA" refers to a DNA that is complementary to and synthesized from an mRNA template using the enzyme reverse transcriptase. The cDNA can be single-stranded or converted into the double-stranded by using the Klenow fragment of DNA polymerase I. "Sense" RNA refers to RNA transcript that includes mRNA and so can be translated into protein within a cell or in vitro. "Antisense RNA" refers to a RNA transcript that is complementary to all or part of a target primary transcript or mRNA and that blocks expression or transcripts accumulation of a target gene (U.S. Pat. No. 5,107,065). The complementarity of an antisense RNA may be with any part of the specific gene transcript, i.e. at the 5' non-coding sequence, 3' non-coding sequence, introns, or the coding sequence. "Functional RNA" refers to antisense RNA, ribozyme RNA, or other RNA that may not be translated but yet has an effect on cellular processes.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the production of a functional end-product e.g., an mRNA or a protein (precursor or mature).

The term "expression cassette" as used herein, refers to a discrete nucleic acid fragment into which a nucleic acid sequence or fragment can be moved.

Expression or overexpression of a gene involves transcription of the gene and translation of the mRNA into a precursor or mature protein. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression or transcript accumulation of identical or substantially similar foreign or endogenous genes (U.S. Pat. No. 5,231,020). The mechanism of co-suppression may be at the DNA level (such as DNA methylation), at the transcriptional level, or at posttranscriptional level.

Co-suppression constructs in plants previously have been designed by focusing on overexpression of a nucleic acid sequence having homology to an endogenous mRNA, in the sense orientation, which results in the reduction of all RNA having homology to the overexpressed sequence (see Vaucheret et al., Plant J. 16:651-659 (1998); and Gura, Nature 404:804-808 (2000)). The overall efficiency of this phenomenon is low, and the extent of the RNA reduction is widely variable. Recent work has described the use of "hairpin" structures that incorporate all, or part, of an mRNA encoding sequence in a complementary orientation that results in a potential "stem-loop" structure for the expressed RNA (PCT Publication No. WO 99/53050 published on Oct. 21, 1999; and PCT Publication No. WO 02/00904 published on Jan. 3, 2002). This increases the frequency of co-suppression in the recovered transgenic plants. Another variation describes the use of plant viral sequences to direct the suppression, or "silencing", of proximal mRNA encoding sequences (PCT Publication No. WO 98/36083 published on Aug. 20, 1998). Genetic and molecular evidences have been obtained suggesting that dsRNA mediated mRNA cleavage may have been the conserved mechanism underlying these gene silencing phenomena (Elmayan et al., Plant Cell 10:1747-1757 (1998); Galun, In Vitro Cell. Dev. Biol. Plant 41 (2):113-123 (2005); Pickford et al, Cell. Mol. Life Sci. 60 (5):871-882 (2003)).

As stated herein, "suppression" refers to a reduction of the level of enzyme activity or protein functionality (e.g., a phenotype associated with a protein) detectable in a transgenic plant when compared to the level of enzyme activity or protein functionality detectable in a non-transgenic or wild type plant with the native enzyme or protein. The level of enzyme activity in a plant with the native enzyme is referred to herein as "wild type" activity. The level of protein functionality in a plant with the native protein is referred to herein as "wild type" functionality. The term "suppression" includes lower, reduce, decline, decrease, inhibit, eliminate and prevent. This reduction may be due to a decrease in translation of the native mRNA into an active enzyme or functional protein. It may also be due to the transcription of the native DNA into decreased amounts of mRNA and/or to rapid degradation of the native mRNA. The term "native enzyme" refers to an enzyme that is produced naturally in a non-transgenic or wild type cell. The terms "non-transgenic" and "wild type" are used interchangeably herein.

"Altering expression" refers to the production of gene product(s) in transgenic organisms in amounts or proportions that differ significantly from the amount of the gene product(s) produced by the corresponding wild-type organisms (i.e., expression is increased or decreased).

"Transformation" refers to the transfer of a nucleic acid fragment into the genome of a host organism, resulting in genetically stable inheritance. Host organisms containing the transformed nucleic acid fragments are referred to as "transgenic" organisms. The preferred method of soybean cell transformation is the use of particle-accelerated or "gene gun" transformation technology (Klein, T., Nature (London) 327:70-73 (1987); U.S. Pat. No. 4,945,050).

"Transient expression" refers to the temporary expression of often reporter genes such as β-glucuronidase (GUS), fluorescent protein genes GFP, ZS-YELLOW1 N1, AM-CYAN1, DS-RED in selected certain cell types of the host organism in which the transgenic gene is introduced temporally by a transformation method. The transformed materials of the host organism are subsequently discarded after the transient gene expression assay.

Standard recombinant DNA and molecular cloning techniques used herein are well known in the art and are described more fully in Sambrook, J. et al., In Molecular Cloning: A Laboratory Manual; $2^{nd}$ ed.; Cold Spring Harbor Laboratory Press: Cold Spring Harbor, New York, 1989 (hereinafter "Sambrook et al., 1989") or Ausubel, F. M., Brent, R., Kingston, R. E., Moore, D. D., Seidman, J. G., Smith, J. A. and Struhl, K., Eds.; In Current Protocols in Molecular Biology; John Wiley and Sons: New York, 1990 (hereinafter "Ausubel et al., 1990").

"PCR" or "Polymerase Chain Reaction" is a technique for the synthesis of large quantities of specific DNA segments, consisting of a series of repetitive cycles (Perkin Elmer Cetus Instruments, Norwalk, Conn.). Typically, the double stranded DNA is heat denatured, the two primers complementary to the 3' boundaries of the target segment are annealed at low temperature and then extended at an intermediate temperature. One set of these three consecutive steps comprises a cycle.

A "recombinant expression construct" is a plasmid vector or a fragment thereof comprising the instant soybean constitutive promoter. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al., EMBO J. 4:2411-2418 (1985); De Almeida et al., Mol. Gen. Genetics 218:78-86 (1989)), and thus that multiple events must be screened in order to obtain lines displaying the desired expression level and pattern. Such screening may be accomplished by PCR and Southern analysis of DNA, RT-PCR and Northern analysis of mRNA expression, Western analysis of protein expression, or phenotypic analysis.

Metallothioneins are ubiquitous low molecular weight proteins of high metal and sulfur content. They are thought to play roles both in the intracellular fixation of the essential trace elements zinc and copper, in controlling the concentrations of the free ions of these elements, in regulating their flow to their cellular destinations, in neutralizing the harmful influences of exposure to toxic elements such as cadmium and mercury (Kägi and Schäffer, Biochemistry 27 (23):8509-8515 (1988)). Metallothionein gene promoters were cloned and characterized to be constitutive and metal-inducible from mouse (Mueller et al., Genes & Development 2 (4):412-427 (1988)), and from *Drosophila* (Bunch et al., Nucleic Acids Res. 16 (3):1043-1061 (1988)). It is demonstrated herein that the soybean metallothionein gene promoter MTH1 can, in fact, be used as a constitutive promoter to drive efficient expression of transgenes, and that such promoter can be isolated and used by one skilled in the art.

This invention concerns an isolated nucleic acid fragment comprising a constitutive metallothionein gene promoter MTH1. This invention also concerns an isolated nucleic acid fragment comprising a promoter wherein said promoter consists essentially of the nucleotide sequence set forth in SEQ ID NO:1, or said promoter consists essentially of a fragment that is substantially similar and functionally equivalent to the nucleotide sequence set forth in SEQ ID NO:1. A nucleic acid fragment that is functionally equivalent to the instant MTH1 promoter is any nucleic acid fragment that is capable of controlling the expression of a coding sequence or functional RNA in a similar manner to the MTH1 promoter. The expression patterns of MTH1 gene and its promoter are set forth in Examples 1, 2, 7, and 8.

The promoter activity of the soybean genomic DNA fragment SEQ ID NO:1 upstream of the MTH1 protein coding sequence was assessed by linking the fragment to a yellow fluorescence reporter gene, ZS-YELLOW1 N1 (YFP) (Matz et al, Nat. Biotechnol. 17:969-973 (1999)), transforming the promoter:YFP expression cassette into soybean, and analyzing YFP expression in various cell types of the transgenic plants (see Example 7 and 8). YFP expression was detected in all parts of the transgenic plants though stronger expression was detected in fast growing tissues such as developing embryos and pods. These results indicated that the nucleic acid fragment contained a constitutive promoter.

It is clear from the disclosure set forth herein that one of ordinary skill in the art could perform the following procedure:

1) operably linking the nucleic acid fragment containing the MTH1 promoter sequence to a suitable reporter gene; there are a variety of reporter genes that are well known to those skilled in the art, including the bacterial GUS gene, the firefly luciferase gene, and the cyan, green, red, and yellow fluorescent protein genes; any gene for which an easy and reliable assay is available can serve as the reporter gene.

2) transforming a chimeric MTH1 promoter:reporter gene expression cassette into an appropriate plant for expression of the promoter. There are a variety of appropriate plants which can be used as a host for transformation that are well known to those skilled in the art, including the dicots, *Arabidopsis*, tobacco, soybean, oilseed rape, peanut, sunflower, safflower, cotton, tomato, potato, cocoa and the monocots, corn, wheat, rice, barley and palm.

3) testing for expression of the MTH1 promoter in various cell types of transgenic plant tissues, e.g., leaves, roots, flowers, seeds, transformed with the chimeric MTH1 promoter: reporter gene expression cassette by assaying for expression of the reporter gene product.

In another aspect, this invention concerns a recombinant DNA construct comprising at least one heterologous nucleic acid fragment operably linked to any promoter, or combination of promoter elements, of the present invention. Recombinant DNA constructs can be constructed by operably linking the nucleic acid fragment of the invention MTH1 promoter or a fragment that is substantially similar and functionally equivalent to any portion of the nucleotide sequence set forth in SEQ ID NOs:1, 2, 3, 4, 5, or 6 to a heterologous nucleic acid fragment. Any heterologous nucleic acid fragment can be used to practice the invention. The selection will depend upon the desired application or phenotype to be achieved. The various nucleic acid sequences can be manipulated so as to provide for the nucleic acid sequences in the proper orientation. It is believed that various combinations of promoter elements as described herein may be useful in practicing the present invention.

In another aspect, this invention concerns a recombinant DNA construct comprising at least one acetolactate synthase (ALS) nucleic acid fragment operably linked to MTH1 promoter, or combination of promoter elements, of the present invention. The acetolactate synthase gene is involved in the biosynthesis of branched chain amino acids in plants and is the site of action of several herbicides including sulfonyl urea. Expression of a mutated acetolactate synthase gene encoding a protein that can no longer bind the herbicide will enable the transgenic plants to be resistant to the herbicide (U.S. Pat. No. 5,605,011, U.S. Pat. No. 5,378,824). The mutated acetolactate synthase gene is also widely used in plant transformation to select transgenic plants.

In another embodiment, this invention concerns host cells comprising either the recombinant DNA constructs of the invention as described herein or isolated polynucleotides of the invention as described herein. Examples of host cells which can be used to practice the invention include, but are not limited to, yeast, bacteria, and plants.

Plasmid vectors comprising the instant recombinant expression construct can be constructed. The choice of plasmid vector is dependent upon the method that will be used to transform host cells. The skilled artisan is well aware of the genetic elements that must be present on the plasmid vector in order to successfully transform, select and propagate host cells containing the chimeric gene.

Methods for transforming dicots, primarily by use of *Agrobacterium tumefaciens*, and obtaining transgenic plants have been published, among others, for cotton (U.S. Pat. No. 5,004,863, U.S. Pat. No. 5,159,135); soybean (U.S. Pat. No. 5,569,834, U.S. Pat. No. 5,416,011); Brassica (U.S. Pat. No. 5,463,174); peanut (Cheng et al., Plant Cell Rep. 15:653-657 (1996), McKently et al., Plant Cell Rep. 14:699-703 (1995)); papaya (Ling et al., Bio/technology 9:752-758 (1991)); and pea (Grant et al., Plant Cell Rep. 15:254-258 (1995)). For a review of other commonly used methods of plant transformation see Newell, C. A., Mol. Biotechnol. 16:53-65 (2000). One of these methods of transformation uses *Agrobacterium rhizogenes* (Tepfler, M. and Casse-Delbart, F., Microbiol. Sci. 4:24-28 (1987)). Transformation of soybeans using direct delivery of DNA has been published using PEG fusion (PCT Publication No. WO 92/17598), electroporation (Chowrira et al., Mol. Biotechnol. 3:17-23 (1995); Christou et al., Proc. Natl. Acad. Sci. U.S.A. 84:3962-3966 (1987)), microinjection, or particle bombardment (McCabe et al., BiolTechnology 6:923 (1988); Christou et al., Plant Physiol. 87:671-674 (1988)).

There are a variety of methods for the regeneration of plants from plant tissues. The particular method of regeneration will depend on the starting plant tissue and the particular plant species to be regenerated. The regeneration, development and cultivation of plants from single plant protoplast transformants or from various transformed explants is well known in the art (Weissbach and Weissbach, Eds.; In Methods for Plant Molecular Biology; Academic Press, Inc.: San Diego, Calif., 1988). This regeneration and growth process typically includes the steps of selection of transformed cells, culturing those individualized cells through the usual stages of embryonic development or through the rooted plantlet stage. Transgenic embryos and seeds are similarly regenerated. The resulting transgenic rooted shoots are thereafter planted in an appropriate plant growth medium such as soil. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present invention containing a desired polypeptide is cultivated using methods well known to one skilled in the art.

In addition to the above discussed procedures, practitioners are familiar with the standard resource materials which describe specific conditions and procedures for the construction, manipulation and isolation of macromolecules (e.g., DNA molecules, plasmids, etc.), generation of recombinant DNA fragments and recombinant expression constructs and the screening and isolating of clones, (see for example, Sambrook, J. et al., In Molecular Cloning: A Laboratory Manual; $2^{nd}$ ed.; Cold Spring Harbor Laboratory Press: Cold Spring Harbor, New York, 1989; Maliga et al., In Methods in Plant Molecular Biology; Cold Spring Harbor Press, 1995; Birren et al., In Genome Analysis: Detecting Genes, 1; Cold Spring Harbor: New York, 1998; Birren et al., In Genome Analysis: Analyzing DNA, 2; Cold Spring Harbor: New York, 1998; Clark, Ed., In Plant Molecular Biology: A Laboratory Manual; Springer: New York, 1997).

The skilled artisan will also recognize that different independent transformation events will result in different levels and patterns of expression of the chimeric genes (Jones et al., EMBO J. 4:2411-2418 (1985); De Almeida et al., Mol. Gen. Genetics 218:78-86 (1989)). Thus, multiple events must be screened in order to obtain lines displaying the desired expression level and pattern. Such screening may be accomplished by Northern analysis of mRNA expression, Western analysis of protein expression, or phenotypic analysis. Also of interest are seeds obtained from transformed plants displaying the desired gene expression profile.

The level of activity of the MTH1 promoter is comparable to that of many known strong promoters, such as the CaMV 35S promoter (Atanassova et al., Plant Mol. Biol. 37:275-285 (1998); Battraw and Hall, Plant Mol. Biol. 15:527-538 (1990); Holtorf et al., Plant Mol. Biol. 29:637-646 (1995); Jefferson et al., EMBO J. 6:3901-3907 (1987); Wilmink et al., Plant Mol. Biol. 28:949-955 (1995)), the *Arabidopsis* oleosin promoters (Plant et al., Plant Mol. Biol. 25:193-205 (1994); Li, Texas A&M University Ph.D. dissertation, pp. 107-128 (1997)), the *Arabidopsis* ubiquitin extension protein promoters (Callis et al., J. Biol. Chem. 265(21):12486-12493 (1990)), a tomato ubiquitin gene promoter (Rollfinke et al., Gene 211:267-276 (1998)), a soybean heat shock protein promoter, and a maize H3 histone gene promoter (Atanassova et al., Plant Mol. Biol. 37:275-285 (1998)). Universal expression of chimeric genes in most plant cells makes the MTH1 promoter of the instant invention especially useful when constitutive expression of a target heterologous nucleic acid fragment is required.

Another general application of the MTH1 promoter of the invention is to construct chimeric genes that can be used to reduce expression of at least one heterologous nucleic acid fragment in a plant cell. To accomplish this, a chimeric gene designed for gene silencing of a heterologous nucleic acid fragment can be constructed by linking the fragment to the MTH1 promoter of the present invention. (See U.S. Pat. No. 5,231,020, and PCT Publication No. WO 99/53050 published on Oct. 21, 1999, PCT Publication No. WO 02/00904 published on Jan. 3, 2002, and PCT Publication No. WO 98/36083 published on Aug. 20, 1998, for methodology to block plant gene expression via cosuppression.) Alternatively, a chimeric gene designed to express antisense RNA for a heterologous nucleic acid fragment can be constructed by linking the fragment in reverse orientation to the MTH1 promoter of the present invention. (See U.S. Pat. No. 5,107,065 for methodology to block plant gene expression via antisense RNA.) Either the cosuppression or antisense chimeric gene can be introduced into plants via transformation. Transformants wherein expression of the heterologous nucleic acid fragment is decreased or eliminated are then selected.

This invention also concerns a method of altering (increasing or decreasing) the expression of at least one heterologous nucleic acid fragment in a plant cell which comprises:
(a) transforming a plant cell with the recombinant expression construct described herein;
(b) growing fertile mature plants from the transformed plant cell of step (a);
(c) selecting plants containing a transformed plant cell wherein the expression of the heterologous nucleic acid fragment is increased or decreased.

Transformation and selection can be accomplished using methods well-known to those skilled in the art including, but not limited to, the methods described herein.

EXAMPLES

The present invention is further defined in the following Examples, in which parts and percentages are by weight and degrees are Celsius, unless otherwise stated. Sequences of promoters, cDNA, adaptors, and primers listed in this invention all are in the 5' to 3' orientation unless described otherwise. Techniques in molecular biology were typically performed as described in Ausubel, F. M. et al., In Current Protocols in Molecular Biology; John Wiley and Sons: New York, 1990 or Sambrook, J. et al., In Molecular Cloning: A Laboratory Manual; $2^{nd}$ ed.; Cold Spring Harbor Laboratory Press: Cold Spring Harbor, New York, 1989 (hereinafter "Sambrook et al., 1989"). It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

The disclosure of each reference set forth herein is incorporated herein by reference in its entirety.

Example 1

Identification of Soybean Constitutive Promoter Candidate Genes

Soybean expression sequence tags (EST) were generated by sequencing randomly selected clones from cDNA libraries constructed from different soybean tissues. Multiple EST sequences could often be found with different lengths representing the different regions of the same soybean gene. If more EST sequences representing the same gene are more frequently found from a tissue-specific cDNA library such as a flower library than from a leaf library, there is a possibility that the represented gene could be a flower preferred gene candidate. Likewise, if similar numbers of ESTs for the same gene were found in various libraries constructed from different tissues, the represented gene could be a constitutively expressed gene. Multiple EST sequences representing the same soybean gene could be compiled electronically based on their overlapping sequence homology into a unique full length sequence representing the gene. These assembled unique gene sequences were accumulatively collected in Pioneer Hi-Bred Int'l proprietary searchable databases. To identify strong constitutive promoter candidate genes, searches were performed to look for gene sequences that were found at similar frequencies in leaf, root, flower, embryos, pod, and also in other libraries. One unique gene PSO333209 was identified in the search to be a constitutive gene candidate. PSO333209 cDNA sequence (SEQ ID NO:15) as well as its putative translated protein sequence (SEQ ID NO:16) were used to search National Center for Biotechnology Information (NCBI) databases. Both PSO333209 nucleotide and amino acid sequences were found to have high homology to metallothionein genes discovered in several plant species including soybean. (NCBI Accession No. AB176559 (GI47076853, locus AB176559, SEQ ID NO: 45) and NCBI Accession No. BAD18377.1 (GI:47076854, locus BAS18377; SEQ ID NO: 46).

Example 2

Quantitative RT-PCR Profiles of MTH1 Gene Expression in Soybean

The expression profile of PSO333209 was confirmed and extended by analyzing 14 different soybean tissues using the relative quantitative RT-PCR technique with a ABI7500 real time PCR system (Applied Biosystems, Foster City, Calif.). Fourteen soybean tissues, somatic embryo, somatic embryo one week on charcoal plate, leaf, leaf petiole, root, flower bud, open flower, R3 pod, R4 seed, R4 pod coat, R5 seed, R5 pod coat, R6 seed, R6 pod coat were collected from cultivar 'Jack' and flash frozen in liquid nitrogen. The seed and pod development stages were defined according to descriptions in Fehr and Caviness, IWSRBC 80:1-12 (1977). Total RNA was extracted with TRizol® reagents (Invitrogen, Carlsbad, Calif.) and treated with DNase I to remove any trace amount of genomic DNA contamination. The first strand cDNA was synthesized using the Superscript™ III reverse transcriptase (Invitrogen). Regular PCR analysis was done to confirm that the cDNA was free of any genomic DNA using primers shown in SEQ ID NO:20 and 21. The primers are specific to the 5'UTR intron/exon junction regions of a soybean S-adenosylmethionine synthetase gene promoter SAMS (Falco and Li, WO 00/37662 (2000)). PCR using this primer set will amplify a 967 bp DNA fragment from any soybean genomic DNA template and a 376 bp DNA fragment from the cDNA template. Genome DNA-free cDNA aliquots were used in quantitative RT-PCR analysis in which an endogenous soybean ATP sulfurylase gene was used as an internal control and wild type soybean genomic DNA was used as the calibrator for relative quantification. PSO33209 gene-specific primers SEQ ID NO:22 and 23 and ATP sulfurylase (ATPS) gene-specific primers SEQ ID NO:24 and 25 were used in separate PCR reactions using the Power Sybr® Green real time PCR master mix (Applied Biosystems). PCR reaction data were captured and analyzed using the sequence detection software provided with the ABI7500 real time PCR system. The qRT-PCR profiling of the PSO333209 MTH1 gene expression confirmed its strong and constitutive expression pattern (FIG. 1).

Example 3

Isolation of Soybean MTH1 Promoter

A BAC clone SBH85K11 corresponding to PSO333268 was identified from the screening of Pioneer Hi-Bred Int'l propriety soybean BAC libraries using PSO333209 gene-specific primers SEQ ID NO:26 and 27 by PCR (polymerase chain reaction). The BAC clone was partially sequenced to reveal an approximately 2 Kb sequence upstream of PSO333209 MTH1 gene coding region. The primers shown in SEQ ID NO:7 and 8 were then designed to amplify the putative full length 1658 bp MTH1 promoter from the BAC clone DNA by PCR. SEQ ID NO:7 contains a recognition site for the restriction enzyme XmaI. SEQ ID NO:8 contains a recognition site for the restriction enzyme NcoI. In order to study promoter function, the MTH 1 promoter was cloned into an expression vector via the restriction enzymes sites.

PCR cycle conditions were 94° C. for 4 minutes; 35 cycles of 94° C. for 30 seconds, 60° C. for 1 minute, and 68° C. for 2 minutes; and a final 68° C. for 5 minutes before holding at 4° C. using the Platinum high fidelity Taq DNA polymerase (Invitrogen). The PCR reaction was resolved using agarose gel electrophoresis to identify the right size PCR product representing the ~1.6 Kb MTH1 promoter. The PCR amplified DNA of the correct size was then digested with XmaI and NcoI restriction enzymes and the fragment was cloned into a GATEWAY® (Invitrogen) cloning entry vector by conventional ligation to place the putative MTH1 promoter upstream of the ZS-YELLOW N1 fluorescent reporter gene (YFP). Several clones containing the ~1.6 Kb DNA insert were sequenced and construct QC371 (FIG. 3, SEQ ID NO:17) was confirmed to contain the identical MTH1 promoter sequence as previously sequenced from the BAC clone SBH85K11. The MTH1 promoter sequence is herein listed as SEQ ID NO:1.

Example 4

MTH1 Promoter Copy Number Analysis

Figure 2A:
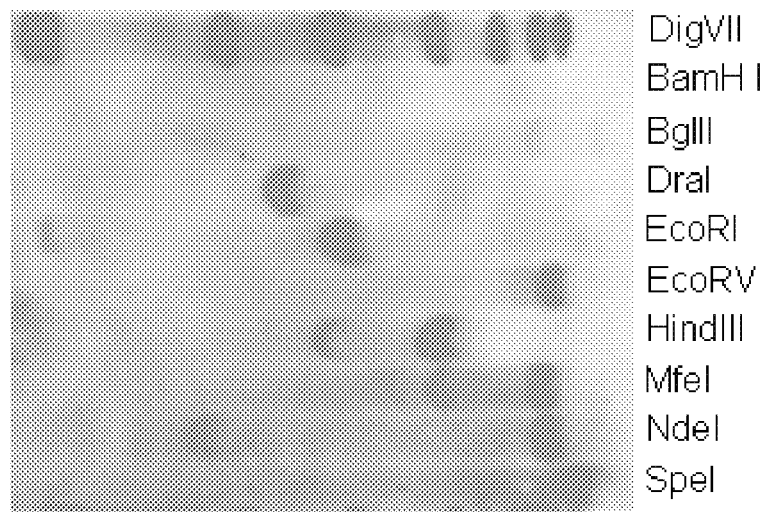
FIG. 2 is MTH1 promoter copy number analysis by Southern.
Figure 2B:
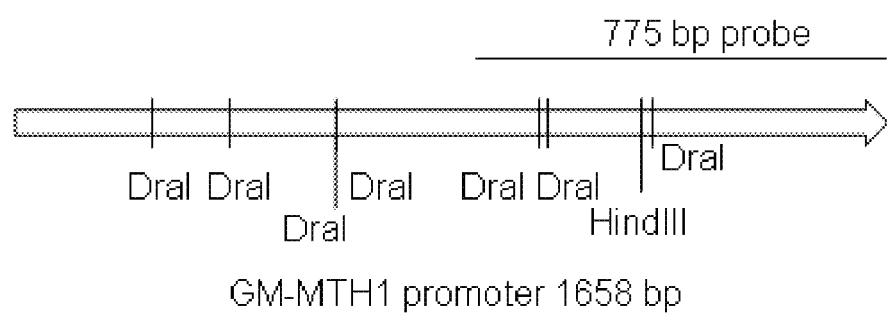

Southern hybridization analysis was performed to examine whether additional copies or sequences with significant similarity to the MTH1 promoter exist in the soybean genome. Soybean 'Jack' wild type genomic DNA was digested with nine different restriction enzymes, BamHI, BgIII, DraI, EcoRI, EcoRV, HindIII, MfeI, NdeI, and SpeI and distributed in a 0.7% agarose gel by electrophoresis. The DNA was blotted onto Nylon membrane and hybridized at 60° C. with digoxigenin labeled MTH1 promoter DNA probe in Easy-Hyb Southern hybridization solution, and then sequentially washed 10 minutes with 2×SSC/0.1% SDS at room temperature and 3×10 minutes at 65° C. with 0.1×SSC/0.1% SDS according to the protocol provided by the manufacturer (Roche Applied Science, Indianapolis, Ind.). The MTH1 promoter probe was labeled by PCR using the DIG DNA labeling kit (Roche Applied Science) with two gene specific primers SEQ ID NO:12 and SEQ ID NO:9 to make a 775 bp long probe corresponding to the 3' end half of the MTH1 promoter (FIG. 2B).

According to the MTH1 promoter sequence, HindIII would cut the 775 bp probe region only once and in the middle to produce a 309 bp 5' end fragment and a 466 bp 3' end fragment. Both fragment would be long enough to be stably hybridized by the probe so two bands were expected for each copy of the MTH1 promoter if digested with HindIII (FIG. 2B). DraI would cut the 1658 bp MTH1 promoter seven times with three cuts in the 775 bp probe region. Only the 3' end 442 bp half was long enough to be stably hybridized so only one band for each copy of MTH1 would be expected if digested with DraI. None of the other seven restriction enzymes BamHI, BgIII, EcoRI, EcoRV, MfeI, NdeI, and SpeI would cut the probe region. Therefore, only one band would be expected to hybridize to the probe for each of the seven different digestions if only one copy of MTH1 sequence exists in the soybean genome (FIG. 2B). The observation that only one band was detected in seven digestions including BgIII, DraI, EcoRI, EcoRV, MfeI, NdeI, and SpeI suggested that there is only one copy of DNA sequence in soybean genome with significant similarity to the MTH1 promoter sequence SE ID NO:1 (FIG. 2A). The observation that no band was detected in the BamHI or HindIII lane suggested that these two digestions failed to produce any MTH1 containing genomic DNA fragment of appropriate sizes that could be retained on the Southern blot. The largest band and smallest band of the molecular markers on the Southern blot are 8576 bp and 1882 bp, respectively.

Example 5

MTH1:YFP Reporter Gene Constructs and Soybean Transformation

Figure 3:
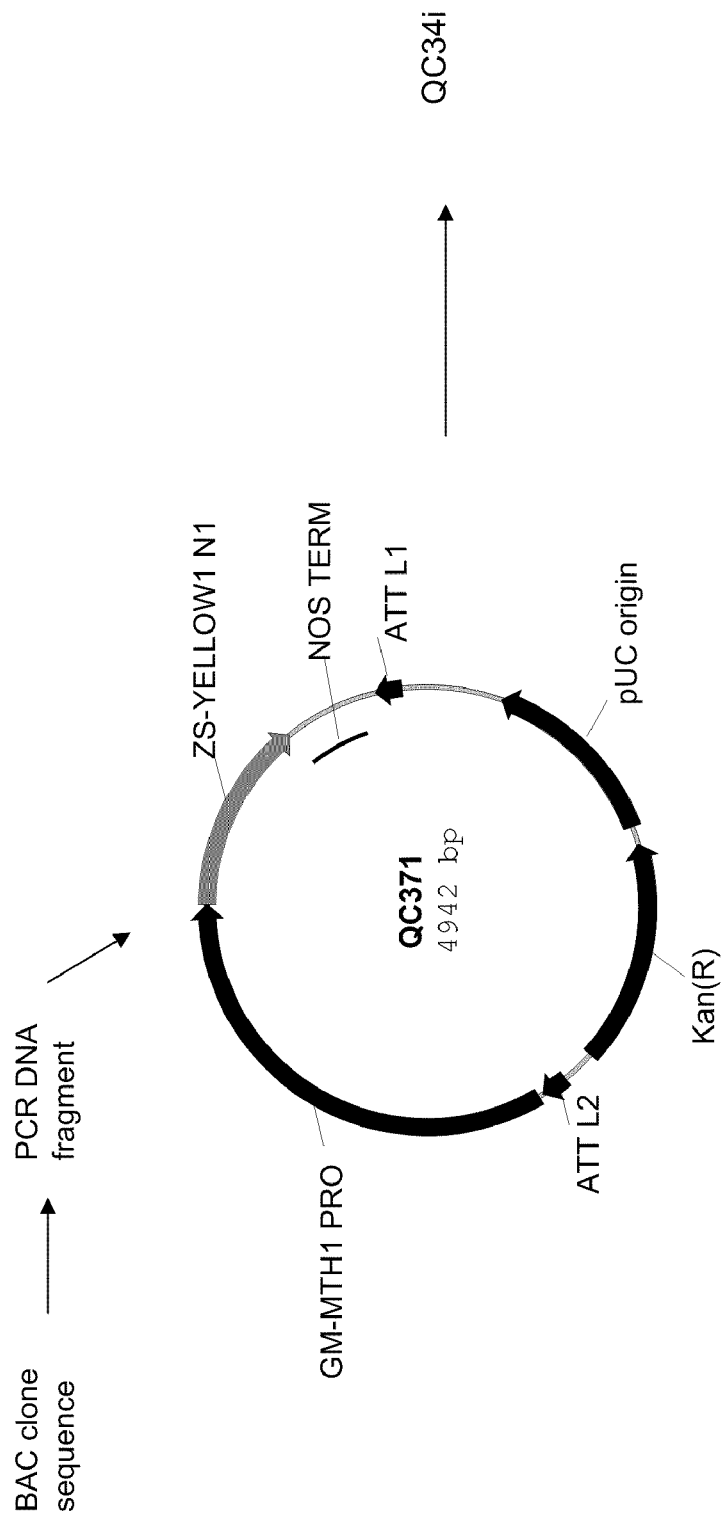
FIG. 3A-3B shows the maps of plasmid QC371, QC324i, and QC383.
Figure 3:
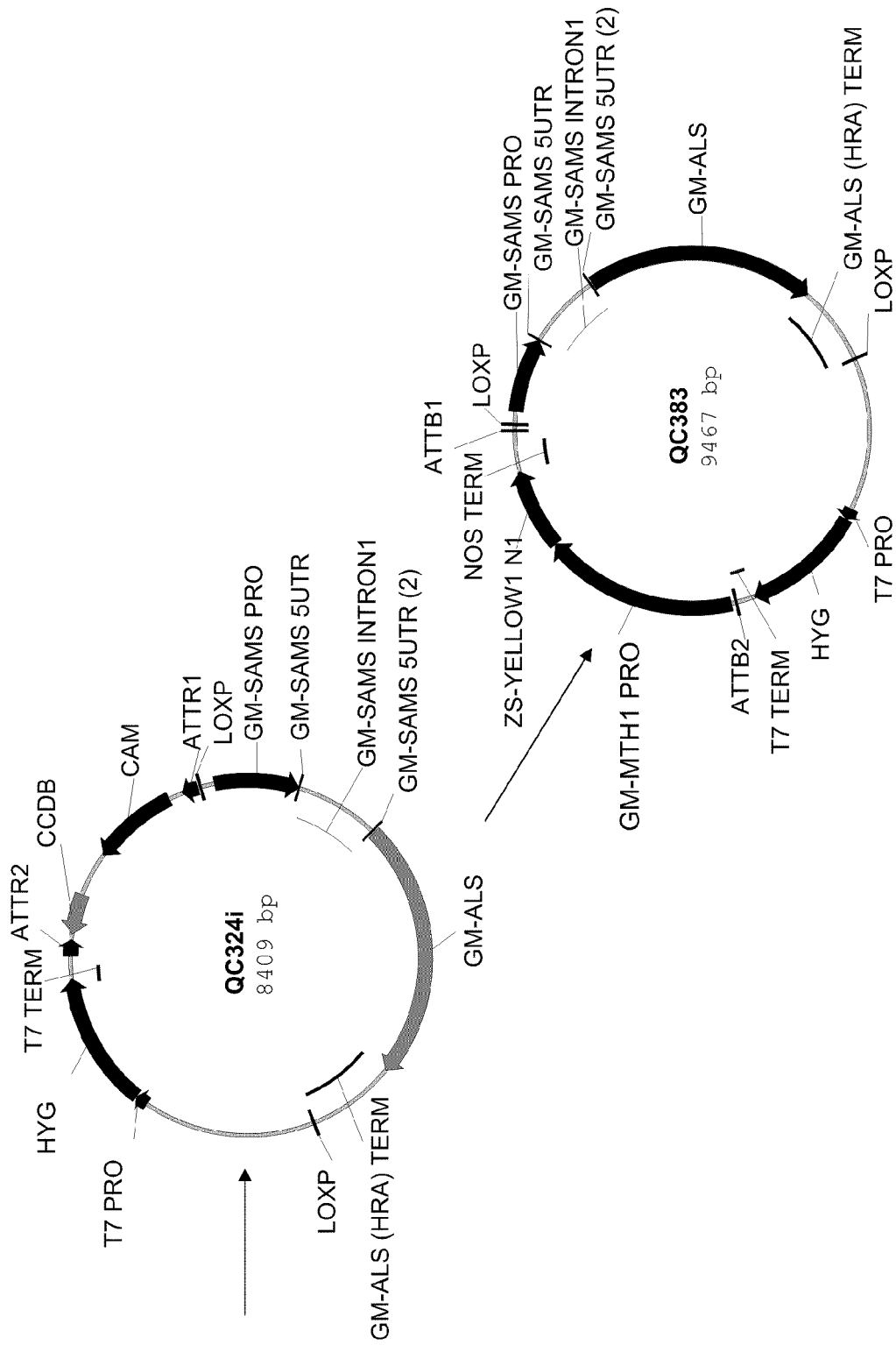

The MTH1:YFP expression cassette in GATEWAY® entry construct QC371 (SEQ ID NO:17) described in EXAMPLE 3 was moved into a GATEWAY® destination vector QC324i (SEQ ID NO:43) by LR Clonase® mediated DNA recombination between the attL1 and attL2 recombination sites (SEQ ID NO:37, and 38, respectively) in QC371 and the attR1-attR2 recombination sites (SEQ ID NO:39, and 40, respectively) in QC324i (Invitrogen). Since the destination vector QC324i already contains a soybean transformation selectable marker gene SAMS:ALS, the resulting DNA construct QC383 (SEQ ID NO:18) has two gene expression cassettes MTH1:YFP and SAMS:ALS linked together (FIG. 3). Two 21 bp recombination sites attB1 and attB2 (SEQ ID NO:41, and 42, respectively) were newly created recombination sites resulting from DNA recombination between attL1 and attR1, and between attL2 and attR2, respectively. The 6953 bp DNA fragment containing the linked MTH1:YFP and SAMS:ALS expression cassettes was isolated from plasmid QC383 (SEQ ID NO:18) with AscI digestion, separated from the vector backbone fragment by agarose gel electrophoresis, and purified from the gel with a DNA gel extraction kit (QIAGEN®, Valencia, Calif.). The purified DNA fragment was transformed to soybean cultivar Jack by the method of particle gun bombardment (Klein et al., Nature 327:70-73 (1987); U.S. Pat. No. 4,945,050) as described in detail below to study the MTH1 promoter activity in stably transformed soybean plants.

The same methodology as outlined above for the MTH1:YFP expression cassette construction and transformation can be used with other heterologous nucleic acid sequences encoding for example a reporter protein, a selection marker, a protein conferring disease resistance, protein conferring herbicide resistance, protein conferring insect resistance; protein involved in carbohydrate metabolism, protein involved in fatty acid metabolism, protein involved in amino acid metabolism, protein involved in plant development, protein involved in plant growth regulation, protein involved in yield improvement, protein involved in drought resistance, protein involved in cold resistance, protein involved in heat resistance and salt resistance in plants.

Soybean somatic embryos from the Jack cultivar were induced as follows. Cotyledons (~3 mm in length) were dissected from surface sterilized, immature seeds and were cultured for 6-10 weeks in the light at 26° C. on a Murashige and Skoog media containing 0.7% agar and supplemented with 10 mg/ml 2,4-D (2,4-Dichlorophenoxyacetic acid). Globular stage somatic embryos, which produced secondary embryos, were then excised and placed into flasks containing liquid MS medium supplemented with 2,4-D (10 mg/ml) and cultured in the light on a rotary shaker. After repeated selection for clusters of somatic embryos that multiplied as early, globular staged embryos, the soybean embryogenic suspension cultures were maintained in 35 ml liquid media on a rotary shaker, 150 rpm, at 26° C. with fluorescent lights on a 16:8 hour day/night schedule. Cultures were subcultured every two weeks by inoculating approximately 35 mg of tissue into 35 ml of the same fresh liquid MS medium.

Soybean embryogenic suspension cultures were then transformed by the method of particle gun bombardment using a DuPont Biolistic™ PDS1000/HE instrument (Bio-Rad Laboratories, Hercules, Calif.). To 50 µl of a 60 mg/ml 1.0 mm gold particle suspension were added (in order): 30 µl of 30 ng/µl QC383 DNA fragment MTH1:YFP+SAMS:ALS, 20 µl of 0.1 M spermidine, and 25 µl of 5 M CaCl$_2$. The particle preparation was then agitated for 3 minutes, spun in a centrifuge for 10 seconds and the supernatant removed. The DNA-coated particles were then washed once in 400 µl 100% ethanol and resuspended in 45 µl of 100% ethanol. The DNA/particle suspension was sonicated three times for one second each. 5 µl of the DNA-coated gold particles was then loaded on each macro carrier disk.

Approximately 300-400 mg of a two-week-old suspension culture was placed in an empty 60×15 mm Petri dish and the residual liquid removed from the tissue with a pipette. For each transformation experiment, approximately 5 to 10 plates of tissue were bombarded. Membrane rupture pressure was set at 1100 psi and the chamber was evacuated to a vacuum of 28 inches mercury. The tissue was placed approximately 3.5 inches away from the retaining screen and bombarded once. Following bombardment, the tissue was divided in half and placed back into liquid media and cultured as described above.

Five to seven days post bombardment, the liquid media was exchanged with fresh media containing 100 ng/ml chlorsulfuron as selection agent. This selective media was refreshed weekly. Seven to eight weeks post bombardment, green, transformed tissue was observed growing from untransformed, necrotic embryogenic clusters. Isolated green tissue was removed and inoculated into individual flasks to generate new, clonally propagated, transformed embryogenic suspension cultures. Each clonally propagated culture was treated as an independent transformation event and subcultured in the same liquid MS media supplemented with 2,4-D (10 mg/ml) and 100 ng/ml chlorsulfuron selection agent to increase mass. The embryogenic suspension cultures were then transferred to agar solid MS media plates without 2,4-D supplement to allow somatic embryos to develop. A sample of each event was collected at this stage for quantitative PCR analysis.

Cotyledon stage somatic embryos were dried-down (by transferring them into an empty small Petri dish that was seated on top of a 10 cm Petri dish containing some agar gel to allow slow dry down) to mimic the last stages of soybean seed development. Dried-down embryos were placed on germination solid media and transgenic soybean plantlets were regenerated. The transgenic plants were then transferred to soil and maintained in growth chambers for seed production.

Genomic DNA were extracted from somatic embryo samples and analyzed by quantitative PCR using the 7500 real time PCR system (Applied Biosystems) with gene-specific primers and FAM-labeled fluorescence probes to check copy numbers of both the SAMS:ALS expression cassette and the MTH1:YFP expression cassette. The qPCR analysis was done in duplex reactions with a heat shock protein (HSP) gene as the endogenous controls and a transgenic DNA sample with a known single copy of SAMS:ALS or YFP transgene as the calibrator using the relative quantification methodology (Applied Biosystems). The endogenous control HSP probe was labeled with VIC and the target gene SAMS: ALS or YFP probe was labeled with FAM for the simultaneous detection of both fluorescent probes (Applied Biosystems).

The primers and probes used in the qPCR analysis are listed below.
SAMS forward primer: SEQ ID NO:28
FAM labeled SAMS probe: SEQ ID NO:29
SAMS reverse primer: SEQ ID NO:30
YFP forward primer: SEQ ID NO:31
FAM labeled YFP probe: SEQ ID NO:32
YFP reverse primer: SEQ ID NO:33
HSP forward primer: SEQ ID NO:34
VIC labeled HSP probe: SEQ ID NO:35
HSP reverse primer: SEQ ID NO:36

Only transgenic soybean events containing 1 or 2 copies of both the SAMS:ALS expression cassette and the MTH1:YFP expression cassette were selected for further gene expression evaluation and seed production (see Table 1). Events negative for YFP qPCR or with more than 2 copies for the SAMS qPCR were not further followed. YFP expressions are described in detail in EXAMPLE 8 and are also summarized in Table 1

TABLE 1

Relative transgene copy numbers and YFP expression of MTH1:YFP transgenic plants

| Clone ID | YFP expression | YFP qPCR | SAMS qPCR |
| --- | --- | --- | --- |
| 5275.1.3 | + | 1.5 | 0.7 |
| 5275.4.2 | + | 3.3 | 1.1 |
| 5275.7.5 | + | 2.0 | 1.0 |
| 5275.2.1 | + | 1.3 | 1.5 |
| 5275.3.2 | + | 0.5 | 0.7 |
| 5275.6.9 | + | 1.3 | 1.6 |
| 5275.7.7 | + | 1.9 | 2.4 |
| 5275.7.12 | + | 0.9 | 1.5 |
| 5275.7.13 | + | 0.9 | 0.9 |
| 5275.7.16 | + | 0.9 | 0.7 |
| 5275.7.18 | + | 1.4 | 2.2 |
| 5275.7.21 | + | 2.4 | 1.3 |
| 5275.7.25 | + | 1.2 | 1.4 |
| 5275.8.4 | + | 2.9 | 2.1 |
| 5275.2.10 | + | 1.3 | 2.4 |
| 5275.5.1 | + | 1.5 | 1.2 |
| 5275.5.3 | + | 1.7 | 1.0 |
| 5275.6.16 | + | 2.5 | 2.7 |
| 5275.7.28 | + | 2.3 | 1.8 |

Example 6

Construction of MTH1 Promoter Deletion Constructs

Figure 4:
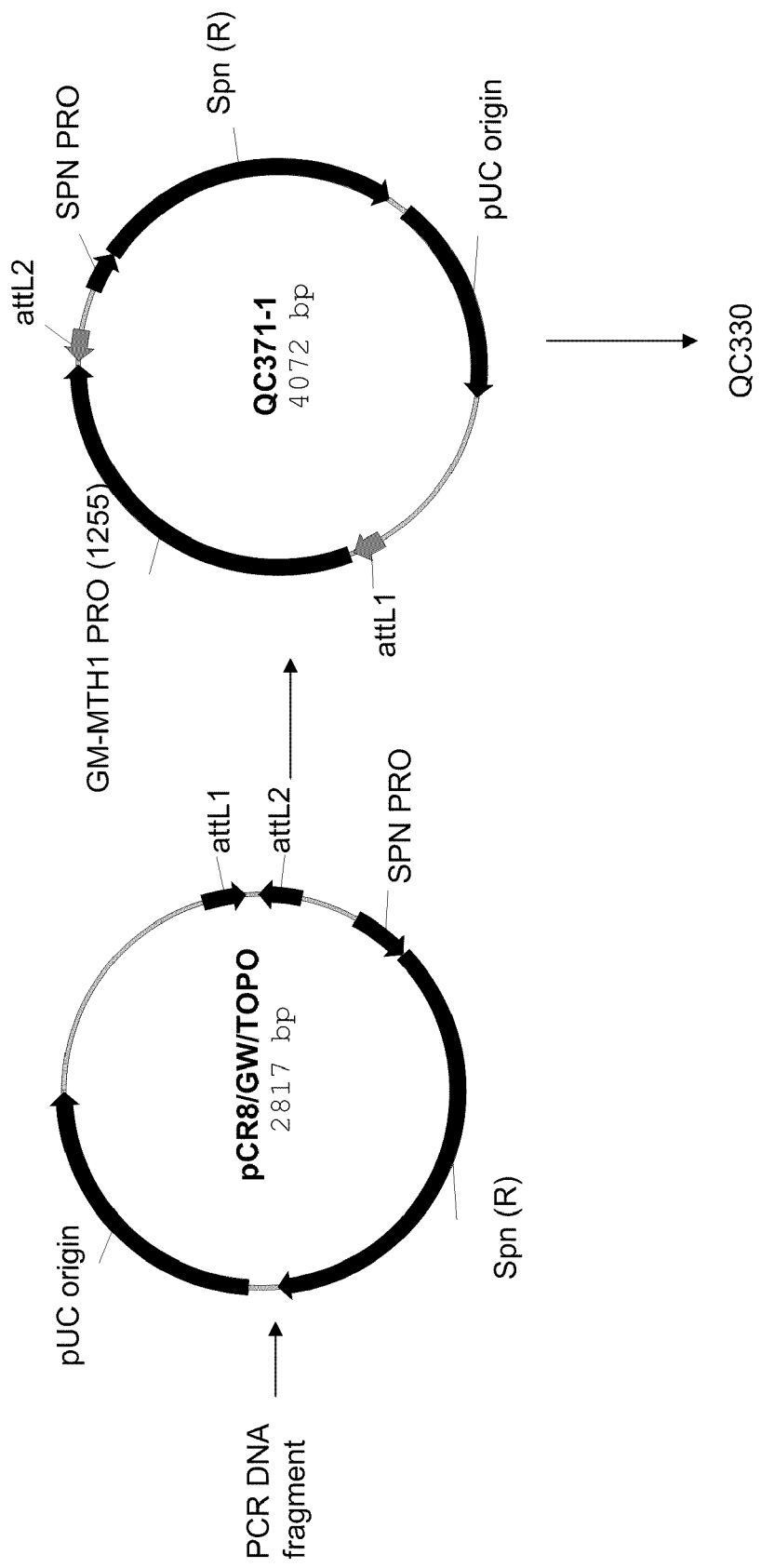
FIG. 4A-4B shows the maps of plasmid pCR8/GW/TOPO, QC371-1, QC300, and QC371-1Y containing the truncated 1255 bp MTH1 promoter. Promoter deletion constructs QC371-2Y, QC371-3Y, QC371-4Y, and QC371-5Y containing the 1003, 775, 513, and 262 bp truncated MTH1 promoters, respectively, have the same map configuration, except for the truncated promoter sequences.
Figure 4:
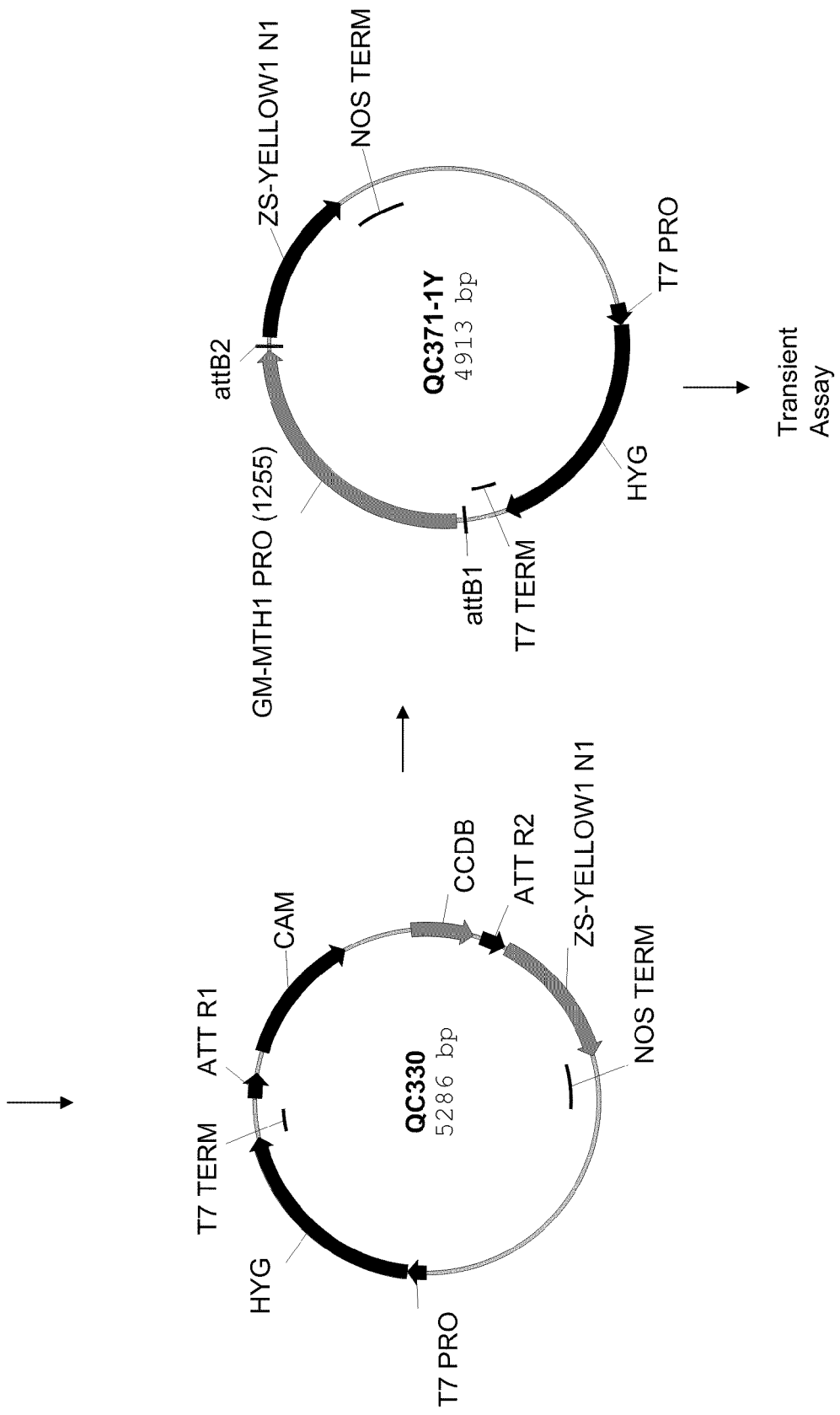
Figure 5:
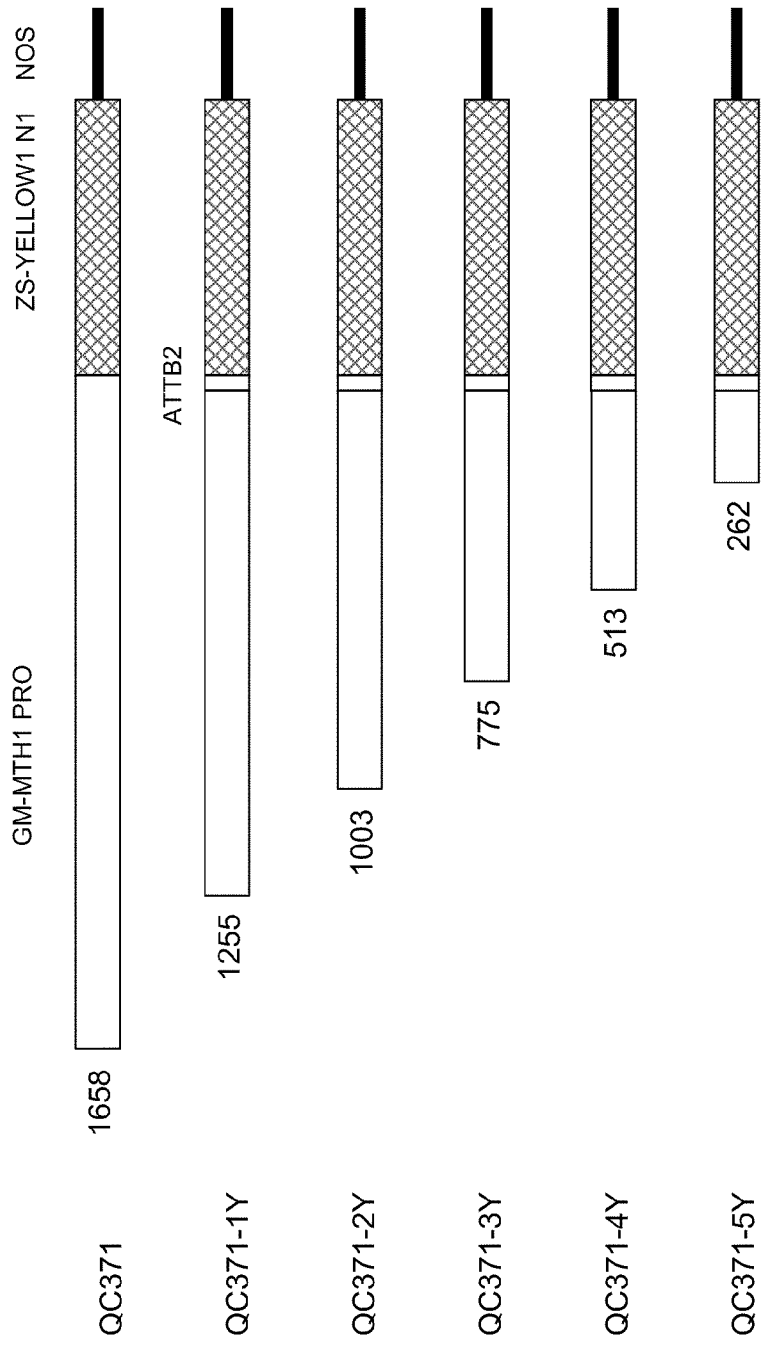
FIG. 5 is the schematic description of the full length construct QC371 and its progressive truncation constructs, QC371-1Y, QC371-2Y, QC371-3Y, QC371-4Y, and QC371-5Y, of the MTH1 promoter. The size of each promoter is given at the left end of each drawing.

To define the transcriptional elements controlling the MTH1 promoter activity, the 1658 bp full length (SEQ ID NO:1) and five 5' unidirectional deletion fragments 1255 bp, 1003 bp, 775 bp, 513 bp, and 262 bp in length corresponding to SEQ ID NO:2, 3, 4, 5, and 6, respectively, were made by PCR amplification from the full length soybean MTH1 promoter contained in the original construct QC371 (FIG. 3A-3B). The same antisense primer (SEQ ID NO:9) was used in the amplification by PCR of all the five MTH1 promoter truncation fragments (SEQ ID NO: 2, 3, 4, 5, and 6) by pairing with different sense primers SEQ ID NOs:10, 11, 12, 13, and 14, respectively. Each of the PCR amplified promoter DNA fragments was cloned into the GATEWAY® cloning ready TA cloning vector pCR8/GW/TOPO (Invitrogen) and clones with the correct orientation, relative to the GATEWAY® recombination sites attL1 and attL2, were selected by BamHI+XhoI double restriction enzymes digestion analysis and sequence confirmation. The map of construct QC371-1 containing the MTH1 promoter fragment SEQ ID NO:2 is shown in FIG. 4A. The maps of constructs QC371-2, 3, 4, and 5 containing the MTH1 promoter fragments SEQ ID NOs:3, 4, 5, and 6 are similar to QC371-1 map and are not shown. The promoter fragment in the right orientation was subsequently cloned into a GATEWAY® destination vector QC330 (SEQ ID NO:44) by GATEWAY® LR Clonase® reaction (Invitrogen) to place the promoter fragment in front of the reporter gene YFP (see the example map QC371-1Y in FIG. 4B). A 21 bp GATEWAY® recombination site attB2 SEQ ID NO:42 was inserted between the promoter and the YFP reporter gene coding region as a result of the GATEWAY® cloning process. The maps of constructs QC371-2Y, 3Y, 4Y, and 5Y containing the MTH1 promoter fragments SEQ ID NOs: 3, 4, 5, and 6 are similar to QC371-1Y map and not shown. The MTH1: YFP promoter deletion constructs were delivered into germinating soybean cotyledons by gene gun bombardment for transient gene expression study. The full length MTH1 promoter in QC371 that does not have the attB2 site located between the promoter and the YFP gene was also included for transient expression analysis. The six MTH1 promoter fragments analyzed are schematically described in FIG. 5.

Example 7

Transient Expression Analysis of MTH1:YFP Constructs

The constructs containing the full length and truncated MTH1 promoter fragments (QC371, QC371-1Y, 2Y, 3Y, 4Y, and 5Y) were tested by transiently expressing the ZS-YELLOW1 N1 (YFP) reporter gene in germinating soybean cotyledons. Soybean seeds were rinsed with 10% TWEEN® 20 in sterile water, surface sterilized with 70% ethanol for 2 minutes and then by 6% sodium hypochloride for 15 minutes. After rinsing the seeds were placed on wet filter paper in Petri dish to germinate for 4-6 days under light at 26° C. Green cotyledons were excised and placed inner side up on a 0.7% agar plate containing Murashige and Skoog media for particle gun bombardment. The DNA and gold particle mixtures were prepared similarly as described in EXAMPLE 5 except with more DNA (100 ng/µl). The bombardments were also carried out under similar parameters as described in EXAMPLE 5. YFP expression was checked under a Leica MZFLIII stereo microscope equipped with UV light source and appropriate light filters (Leica Microsystems Inc., Bannockburn, Ill.) and pictures were taken approximately 24 hours after bombardment with 8× magnification using a Leica DFC500 camera with settings as 0.60 gamma, 1.0× gain, 0.70 saturation, 61 color hue, 56 color saturation, and 0.51 second exposure.

Figure 6:
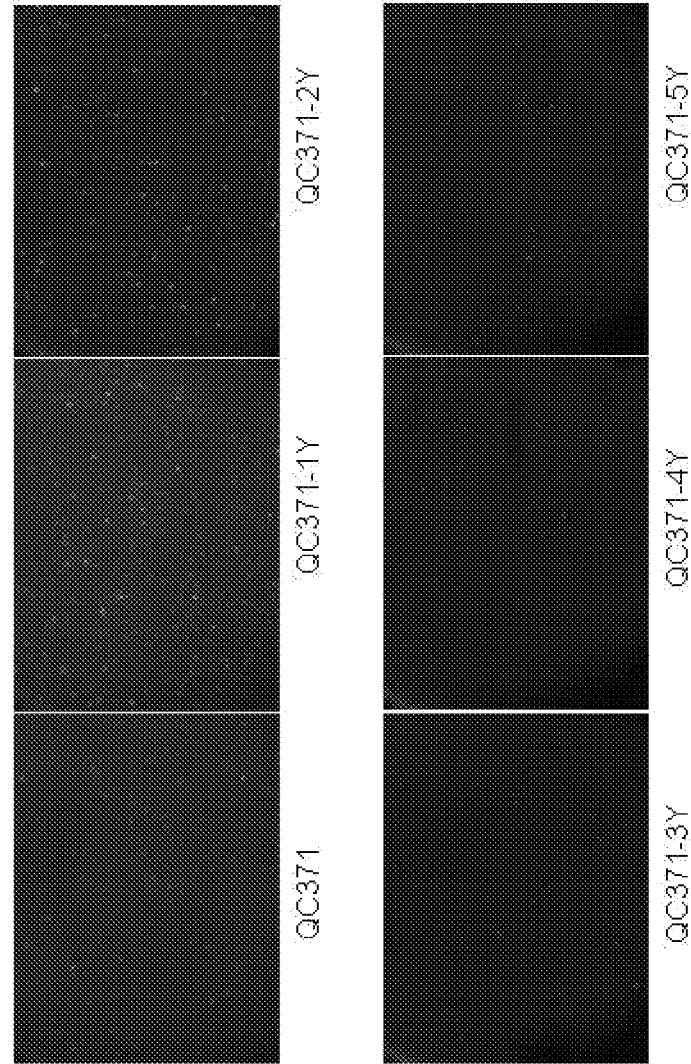
FIG. 6 is the transient expression of the fluorescent protein reporter gene ZS-YELLOW1 N1 in the cotyledons of germinating soybean seeds. The reporter gene is driven by the full length MTH1 promoter in QC371 or by progressively truncated MTH1 promoters in the transient expression constructs QC371-1Y to QC371-5Y.

The full length MTH1 promoter construct QC371, and two deletion constructs QC371-1Y and 2Y had similar moderate yellow fluorescence signals in transient expression assay by showing the large green/yellow dots (shown as bright white dots in FIG. 6). The attB2 site did not seem to interfere with promoter activity and reporter gene expression. Each dot represented a single cotyledon cell which appeared larger if the fluorescence signal was strong or smaller if the fluorescence signal was weak even under the same magnification. The three longer deletions constructs QC371-3Y, 4Y, and 5Y all showed similar though lower levels of YFP gene expression than the full length construct (FIG. 6). The expression of QC371-5Y construct suggested that as short as 262 bp promoter sequence upstream of the start codon ATG was sufficient for the effective expression of a reporter gene by the MTH1 promoter.

Example 8

MTH1:YFP Expression in Stable Transgenic Soybean Plants

Figure 7:
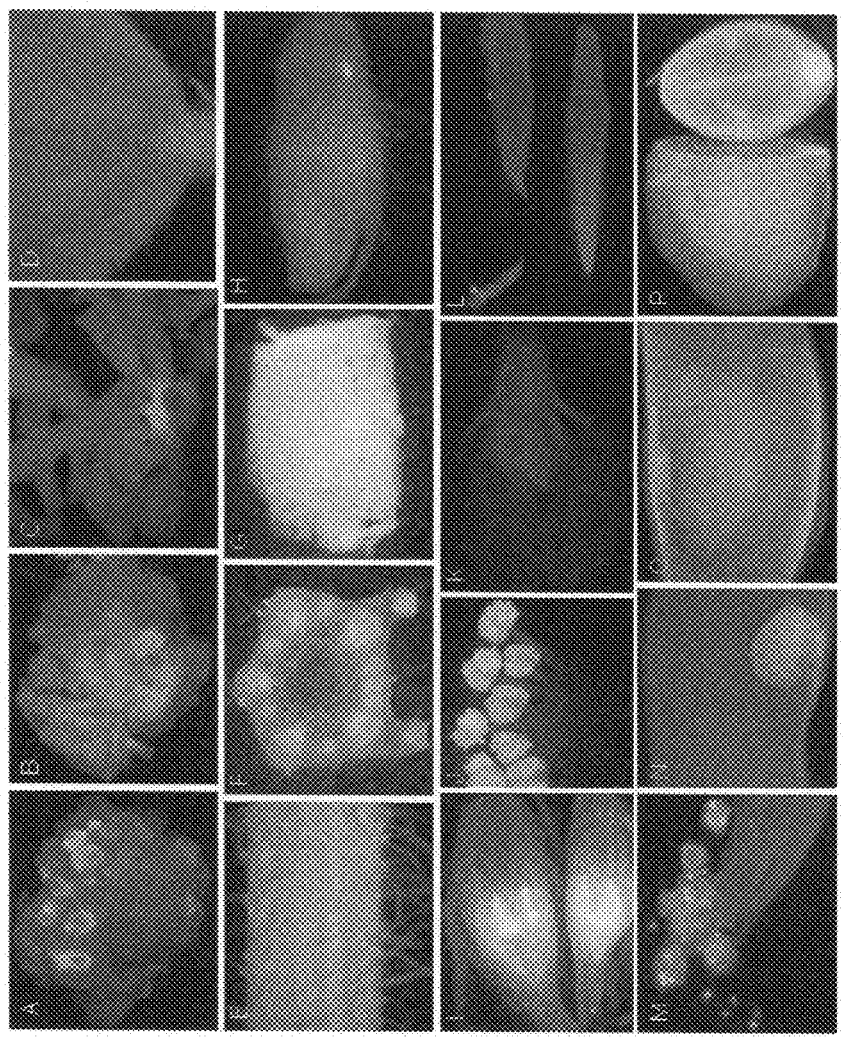
FIG. 7 is the stable expression of the fluorescent protein reporter gene ZS-YELLOW1 N1 in transgenic soybean plants containing a single copy of the transgene construct QC383.

YFP gene expression was tested at different stages of transgenic plant development for yellow fluorescence emission under a Leica MZFLIII stereo microscope equipped with appropriate fluorescent light filters. Yellow fluorescence (shown as bright white areas in FIG. 7) was detected early on during somatic embryo development and throughout all stages of transgenic plant development in all tissues tested, such as somatic embryos, leaf, stem, root, flower, pod, and seed. During tissue culture stages of transgenic plant regeneration, fluorescence was detected in young globular and torpedo stage somatic embryos (FIG. 7A, B), and in mature embryos (FIG. 7C). The negative section of a positive embryo cluster emitted weak red color (shown as dark grey areas in FIG. 7A, B) due to auto fluorescence from the chlorophyll contained in soybean green tissues including embryos. Negative controls for other tissue types displayed in FIG. 7 are not shown, but any green tissue such as leaf or stem negative for YFP expression would be red and any white tissue such as root and petal would be dark yellowish under the yellow fluorescent light filter.

When transgenic plantlets were regenerated from somatic embryos, yellow fluorescence was detected in leaf, stem, and root and was retained in all vegetative tissues throughout mature plants. Fluorescence in young leaves collected from plantlets seemed much stronger than that in leaves collected from mature plants probably partly due to weak masking effect of less chlorophyll in young leaves on yellow fluorescence (FIG. 7D). Fluorescence was readily detected throughout the young stem of plantlets and concentrated in the vascular bundles in the stem of mature plants (FIG. 7E, F). Though trichomes on leaf and stem showed fluorescence, it was difficult to determine if the fluorescence signals were specific to the transgenic reporter gene since trichomes fluoresced under different non-specific fluorescent light filters (FIG. 7D, E). Fluorescence was detected in all parts of root as shown by the cross section of a root (FIG. 7G).

A soybean flower consists of five sepals, five petals including one standard large upper petal, two large side petals, and two small fused lower petals called kneel to enclose ten stamens and one pistil. The pistil consists of a stigma, a style, and an ovary in which there are 2-4 ovules. A stamen consists of a filament, and an anther on its tip. Pollen grains reside inside anther chambers and are released during pollination. The earliest yellow fluorescence was detected in sepals and in the exposed part of petals of a young flower bud when its petals started to outgrow sepals (FIG. 7H). The fluorescence signals seemed to concentrate in anthers when a flower was dissected (FIG. 7I). A close look revealed that the fluorescence signals were strongest in pollen grains at both flower bud stage (FIG. 7J) and open flower stage (FIG. 7M). Signals in other parts of the flower such as petals, style, stigma, pistil wall, and mature anther walls, were mostly too weak to be conclusively called positive (FIG. 7K-M). No fluorescence signal could be detected in the ovules exposed from a pistil (FIG. 7L). The few bright dots on the stigma and pistil wall are pollen grains.

Strong yellow fluorescence was detected in developing pods and seeds at all stages of the MTH1:YFP transgenic plants from very young R3 pod of ~5 mm long, to full R4 pod of ~20 mm long (FIG. 7N), until mature R5, R6 pod fully filled with seeds (FIG. 7O). Detail descriptions of soybean development stages can be found in (Fehr and Caviness, CODEN:IWSRBC 80:1-12 (1977)). Fluorescence signals were detected in both seed coat and embryo especially in the embryonic radical (FIG. 7P). In conclusion, MTH1:YFP expression was detected with high levels in most tissues throughout transgenic plant development indicating that the soybean MTH1 promoter is a constitutive promoter with preferential strong expression in pollen grains.

What is claimed is:

1. An isolated polynucleotide comprising
a nucleotide sequence comprising the sequence set forth in SEQ ID NO:1, wherein said nucleotide sequence is a promoter, or the full-length complement thereof.

2. An isolated polynucleotide comprising a nucleotide sequence comprising a fragment of SEQ ID NO:1 selected from the group consisting of SEQ ID NOs:2-6, wherein said nucleotide sequence is a promoter, or a full-length complement thereof.

3. The isolated polynucleotide of any one of claims 1 or 2 wherein the nucleotide sequence is a constitutive promoter.

4. A recombinant DNA construct comprising the isolated polynucleotide of any one of claims 1, 2, or 3, operably linked to at least one heterologous sequence.

5. A vector comprising the recombinant DNA construct of claim 4.

6. A cell comprising the recombinant DNA construct of claim 4.

7. The cell of claim 6, wherein the cell is a plant cell.

8. A transgenic plant having stably incorporated into its genome the recombinant DNA construct of claim 4.

9. The transgenic plant of claim 8 wherein said plant is a dicot plant.

10. The plant of claim 9 wherein the plant is soybean.

11. Transgenic seed produced by the transgenic plant of claim 9.

12. The recombinant DNA construct according to claim 4, wherein the heterologous sequence codes for a gene selected from the group consisting of: a reporter gene, a selection marker, a disease resistance conferring gene, a herbicide resistance conferring gene, an insect resistance conferring gene; a gene involved in carbohydrate metabolism, a gene involved in fatty acid metabolism, a gene involved in amino acid metabolism, a gene involved in drought resistance, a gene involved in cold resistance, a gene involved in heat resistance and a gene involved in salt resistance in plants.

13. The recombinant DNA construct according to claim 4, wherein the heterologous sequence encodes a protein selected from the group consisting of: a reporter protein, a selection marker, a protein conferring disease resistance, protein conferring herbicide resistance, protein conferring insect resistance, protein involved in carbohydrate metabolism, protein involved in fatty acid metabolism, protein involved in amino acid metabolism, protein involved in drought resistance, protein involved in cold resistance, protein involved in heat resistance and protein involved in salt resistance in plants.

14. A plant stably transformed with a recombinant expression construct comprising:
   (a) a soybean promoter fragment of SEQ ID NO:1 selected from the group consisting of SEQ ID NOs:2-6 and
   (b) a heterologous nucleic acid sequence operably linked to said promoter fragment;
   wherein said promoter fragment is capable of controlling expression of said heterologous nucleic acid fragment in a plant cell.

* * * * *

SEQUENCE LISTING

```
<160> NUMBER OF SEQ ID NOS: 46

<210> SEQ ID NO 1
<211> LENGTH: 1658
<212> TYPE: DNA
<213> ORGANISM: Glycine max

<400> SEQUENCE: 1
gggtgaaatg gaacgtgtgt gatgggtaca agttgcttgt ggtgtatcat gtatgagtat      60
aaaatttagc tcaaataact tatcattgaa cggacttagt tatactttt tttttttta     120 tctttctaat acatatattt cgttgttata aaagtagaaa tgttcgattt ctgtaaaatt     180
atcgttgatt tttcttccac gtaaaataaa attaaaatat gttatatttt tagaacataa     240
caagattcgt gtaaatttaa atttgtgaga atttctaaaa atcaattaaa aatcatcaca     300
aattacagaa aaaccatcat aaattataga ataaaaataa atacaaatac aaattatgat     360 ggttttttaac ctcaaactta aatcttaaat atatttttaa cctttaaaga tatgattttt     420
tggagggcaa aaatatgacc tttcttcaaa gtagtccatt tgtttgtatt tattattaat     480
tgtaaatatt atttttagca ccaaaatatc ttggcataaa attaaaacac acattttttt     540
tctaaggtaa acattaaaaa aagaactcat tccaaaaaag taacatgttt caaaaaatcc     600
aaaaacattt aaattttaaa ataattctag taatagtatt tatatttaat attaaaactc     660
acaaataaat gagattgccc gttttatata aaattgggat gagtaaatat gtatgataca     720
attatataag gacaattaag tataattatg tgtgcatgtt aaagttgatt taattaaata     780
agatgcgtaa attattataa cttttttta acatttatac ttgctaacac accccatatt     840
cacatgataa taggaggcat ctctaatgag ttgatatttt tacacgagag tgatgagtaa     900
gtttgaatta tgcaatcata aatagtaaaa tttaacaatc aatatttatt taccttattt     960
gtaagtgaaa aaaaatattt gtatatatat tataatttaa agtataaatg aatttaaatg    1020
aaatattagg ctgtgaaatt aatcataaga ttcacaaata agaatctaga tgaattaatt    1080
aatacccata gtgaaaaata gtggtctcat taagaaaaaa attgaaaact caagtttatg    1140
ttgtgcactt ttgctatgta agagagagga aaggattaaa atgaaatgag caagctttat    1200
aaaaaaatat aaatttaaaa aaaaaaaaaa aaaaaagca cgaggtagag tagaatgatt    1260
gcatgagtgg cacatggtga caaattcgag acagatattt tcacacccttt ccatcacatc    1320 aactctcccc cgttgatcat catttaatat ctcatccaac ggcaaacaaa cgtacatttt    1380
agaacatacc agaaaatccc tctctctcat caatccaccc aagtgatgaa aacgacgtcg    1440
acgtgggaga agatccgcaa acggattaga cgcgtcgtca gatttcgaca cgtgtacggt    1500
ggatgtttcg gactctctcc cctcaaccgc tttataaatt ggggtcgtgg cttcgccttg    1560
aaactcgttc tagtgtatgt gattgttgtg actcgttctt cttcgtcgtt atcttcttct    1620
tttgttgttt gtgtgtttgt ttttctctc acctgacc                            1658
```

```
<210> SEQ ID NO 2
<211> LENGTH: 1255
<212> TYPE: DNA
<213> ORGANISM: Glycine max

<400> SEQUENCE: 2
ttaaagatat gattttttgg agggcaaaaa tatgaccttt cttcaaagta gtccatttgt      60
ttgtatttat tattaattgt aaatattatt tttagcacca aaatatcttg cataaaatt     120 aaaacacaca ttttttttct aaggtaaaca ttaaaaaaag aactcattcc aaaaaagtaa     180
catgtttcaa aaaatccaaa aacatttaaa ttttaaaata attctagtaa tagtatttat     240
atttaatatt aaaactcaca ataaaatgag attgcccgtt ttatataaaa ttgggatgag     300
taaatatgta tgatacaatt ataaaggac aattaagtat aattatgtgt gcatgttaaa     360
gttgatttaa ttaaataaga tgcgtaaatt attataactt ttttttaaca tttatacttg     420
ctaacacacc ccatattcac atgataatag gaggcatctc taatgagttg atattttta c    480 acgagagtga tgagtaagtt tgaattatgc aatcataaat agtaaaattt aacaatcaat     540
atttatttac cttatttgta agtgaaaaaa aatatttgta tatatattat aatttaaagt     600
ataaatgaat ttaaatgaaa tattaggctg tgaaattaat cataagattc acaaataaga     660
atctagatga attaattaat acccatagtg aaaaatagtg gtctcattaa gaaaaaaatt     720
gaaaactcaa gtttatgttg tgcacttttg ctatgtaaga gagaggaaag gattaaaatg     780
aaatgagcaa gctttataaa aaaatataaa tttaaaaaaa aaaaaaaaaa aaaagcacga     840
ggtagagtag aatgattgca tgagtggcac atggtgacaa attcgagaca gatattttca     900
cacctttcca tcacatcaac tctccccgt tgatcatcat ttaatatctc atccaacggc      960
aaacaaacgt acattttaga acataccaga aaatccctct ctctcatcaa tccacccaag    1020
tgatgaaaac gacgtcgacg tgggagaaga tccgcaaacg gattagacgc gtcgtcagat    1080
ttcgacacgt gtacggtgga tgtttcggac tctctcccct caaccgcttt ataaattggg    1140
gtcgtggctt cgccttgaaa ctcgttctag tgtatgtgat tgttgtgact cgttcttctt    1200
cgtcgttatc ttcttctttt gttgtttgtg tgtttgtttt ttctctcacc tgacc         1255

<210> SEQ ID NO 3
<211> LENGTH: 1003
<212> TYPE: DNA
<213> ORGANISM: Glycine max

<400> SEQUENCE: 3
aactcacaaa taaatgagat tgcccgtttt atataaaatt gggatgagta aatatgtatg      60
atacaattat ataaggacaa ttaagtataa ttatgtgtgc atgttaaagt tgatttaatt     120
aaataagatg cgtaaattat tataactttt ttttaacatt tatacttgct aacacacccc     180
atattcacat gataatagga ggcatctcta atgagttgat attttcacac gagagtgatg     240
agtaagtttg aattatgcaa tcataaatag taaaatttaa caatcaatat ttatttacct     300
tatttgtaag tgaaaaaaa tatttgtata tatattataa tttaaagtat aaatgaattt     360
aaatgaaata ttaggctgtg aaattaatca taagattcac aaataagaat ctagatgaat     420
taattaatac ccatagtgaa aaatagtggt ctcattaaga aaaaattga aaactcaagt      480 ttatgttgtg cacttttgct atgtaagaga gaggaaagga ttaaaatgaa atgagcaagc     540
tttataaaaa aatataaatt taaaaaaaaa aaaaaaaaa aagcacgagg tagagtagaa     600
tgattgcatg agtggcacat ggtgacaaat tcgagacaga tattttcaca cctttccatc     660
acatcaactc tccccgttg atcatcattt aatatctcat ccaacggcaa acaaacgtac      720
```

```
attttagaac ataccagaaa atccctctct ctcatcaatc cacccaagtg atgaaaacga    780
cgtcgacgtg ggagaagatc cgcaaacgga ttagacgcgt cgtcagattt cgacacgtgt    840
acggtggatt tttcggactc tctcccctca accgctttat aaattggggt cgtggcttcg    900
ccttgaaact cgttctagtg tatgtgattg ttgtgactcg ttcttcttcg tcgttatctt    960
cttcttttgt tgtttgtgtg tttgtttttt ctctcacctg acc                     1003

<210> SEQ ID NO 4
<211> LENGTH: 775
<212> TYPE: DNA
<213> ORGANISM: Glycine max

<400> SEQUENCE: 4
acgagagtga tgagtaagtt tgaattatgc aatcataaat agtaaaattt aacaatcaat     60 attatttac cttatttgta agtgaaaaaa aatatttgta tatatattat aatttaaagt    120
ataaatgaat ttaaatgaaa tattaggctg tgaaattaat cataagattc acaataaga    180 atctagatga attaattaat acccatagtg aaaaatagtg gtctcattaa gaaaaaaatt    240
gaaaactcaa gtttatgttg tgcacttttg ctatgtaaga gagaggaaag gattaaaatg    300
aaatgagcaa gctttataaa aaaatataaa tttaaaaaaa aaaaaaaaa aaaagcacga    360 ggtagagtag aatgattgca tgagtggcac atggtgacaa attcgagaca gatattttca    420
cactttccca tcacatcaac tctcccccgt tgatcatcat ttaatatctc atccaacggc    480
aaacaaacgt acattttaga acataccaga aaatccctct ctctcatcaa tccacccaag    540
tgatgaaaac gacgtcgacg tgggagaaga tccgcaaacg gattagacgc gtcgtcagat    600
ttcgacacgt gtacggtgga tgtttcggac tctctcccct caaccgcttt ataaattggg    660
gtcgtggctt cgccttgaaa ctcgttctag tgtatgtgat tgttgtgact cgttcttctt    720
cgtcgttatc ttcttctttt gttgtttgtg tgtttgtttt tctctcacc tgacc         775

<210> SEQ ID NO 5
<211> LENGTH: 513
<212> TYPE: DNA
<213> ORGANISM: Glycine max

<400> SEQUENCE: 5
cacttttgct atgtaagaga gaggaaagga ttaaaatgaa atgagcaagc tttataaaaa     60
aatataaatt taaaaaaaaa aaaaaaaaaa aagcacgagg tagagtagaa tgattgcatg    120
agtggcacat ggtgacaaat tcgagacaga tattttcaca cctttccatc acatcaactc    180
tcccccgttg atcatcattt aatatctcat ccaacggcaa acaaacgtac attttagaac    240
ataccagaaa atccctctct ctcatcaatc cacccaagtg atgaaaacga cgtcgacgtg    300
ggagaagatc cgcaaacgga ttagacgcgt cgtcagattt cgacacgtgt acggtggatg    360
tttcggactc tctcccctca accgctttat aaattggggt cgtggcttcg ccttgaaact    420
cgttctagtg tatgtgattg ttgtgactcg ttcttcttcg tcgttatctt cttcttttgt    480
tgtttgtgtg tttgtttttt ctctcacctg acc                                513

<210> SEQ ID NO 6
<211> LENGTH: 262
<212> TYPE: DNA
<213> ORGANISM: Glycine max

<400> SEQUENCE: 6
tccctctctc tcatcaatcc acccaagtga tgaaaacgac gtcgacgtgg gagaagatcc     60
```

```
gcaaacggat tagacgcgtc gtcagatttc gacacgtgta cggtggatgt ttcggactct    120
ctcccctcaa ccgctttata aattggggtc gtggcttcgc cttgaaactc gttctagtgt    180
atgtgattgt tgtgactcgt tcttcttcgt cgttatcttc ttctttttgtt gtttgtgtgt    240 ttgtttttc tctcacctga cc                                               262
```

<210> SEQ ID NO 7
<211> LENGTH: 34
<212> TYPE: DNA
<213> ORGANISM: Artificial sequence
<220> FEATURE:
<223> OTHER INFORMATION: PSO333209Xma

<400> SEQUENCE: 7

```
atcatcccgg gtgaaatgga acgtgtgtga tggg                                 34
```

<210> SEQ ID NO 8
<211> LENGTH: 37
<212> TYPE: DNA
<213> ORGANISM: Artificial sequence
<220> FEATURE:
<223> OTHER INFORMATION: PSO333209Nco

<400> SEQUENCE: 8

```
ttagtccatg gtcaggtgag agaaaaaaca aacacac                              37
```

<210> SEQ ID NO 9
<211> LENGTH: 26
<212> TYPE: DNA
<213> ORGANISM: Artificial sequence
<220> FEATURE:
<223> OTHER INFORMATION: primer, QC385-A

<400> SEQUENCE: 9

```
ggtcaggtga gagaaaaaac aaacac                                          26
```

<210> SEQ ID NO 10
<211> LENGTH: 27
<212> TYPE: DNA
<213> ORGANISM: Artificial sequence
<220> FEATURE:
<223> OTHER INFORMATION: primer, QC371-S1

<400> SEQUENCE: 10

```
ttaaagatat gattttttgg agggcaa                                         27
```

<210> SEQ ID NO 11
<211> LENGTH: 26
<212> TYPE: DNA
<213> ORGANISM: Artificial sequence
<220> FEATURE:
<223> OTHER INFORMATION: primer, QC371-S2

<400> SEQUENCE: 11

```
aactcacaaa taaatgagat tgcccg                                          26
```

<210> SEQ ID NO 12
<211> LENGTH: 30
<212> TYPE: DNA
<213> ORGANISM: Artificial sequence
<220> FEATURE:
<223> OTHER INFORMATION: primer, QC371-S3

<400> SEQUENCE: 12

```
acgagagtga tgagtaagtt tgaattatgc                                      30
```

<210> SEQ ID NO 13
<211> LENGTH: 29
<212> TYPE: DNA
<213> ORGANISM: Artificial sequence
<220> FEATURE:
<223> OTHER INFORMATION: primer, QC371-S4

<400> SEQUENCE: 13
cacttttgct atgtaagaga gaggaaagg                                      29

<210> SEQ ID NO 14
<211> LENGTH: 24
<212> TYPE: DNA
<213> ORGANISM: Artificial sequence
<220> FEATURE:
<223> OTHER INFORMATION: primer, QC371-S5

<400> SEQUENCE: 14
tccctctctc tcatcaatcc accc                                           24

<210> SEQ ID NO 15
<211> LENGTH: 574
<212> TYPE: DNA
<213> ORGANISM: Glycine max

<400> SEQUENCE: 15
gattgttgtg actcgttctt cttcgtcgtt atcttcttct tttgttgttt gtgtgtttgt     60
tttttctctc acctgaaaat gtcttgctgc ggtggtaact gtggttgcgg aagcgcctgc    120
aagtgcggca acggctgcgg aggctgcaag atgtacccag acttgagcta caccgagtca    180
accaccaccg agaccttggt catgggagtg gcaccagtta aggctcaatt cgagagtgct    240
gaaatgggtg ttcccgctga aacgatggc tgcaaatgtg gagctaactg cacctgcaac    300
ccctgcactt gcaagtgagg tgttggagag ctaaagcttc aagcagaaat ggcccttaga    360
aataatgata aaaactatat gtagtttcaa aacttcaaaa ttatgtagta tgtattatgt    420
tgcactctgg tgttttgtgt ctaaacaaac acccttagaa taaagtggtc atttcttgcc    480
cttgagcaag ttcaagtgtt ttggacttgt gatgggtgtg ttaaggtcat ggttgccttt    540
tttttatata tatatatata tataaatgtt tggt                                574

<210> SEQ ID NO 16
<211> LENGTH: 79
<212> TYPE: PRT
<213> ORGANISM: Glycine max

<400> SEQUENCE: 16

Met Ser Cys Cys Gly Gly Asn Cys Gly Cys Gly Ser Ala Cys Lys Cys
1               5                   10                  15

Gly Asn Gly Cys Gly Gly Cys Lys Met Tyr Pro Asp Leu Ser Tyr Thr
            20                  25                  30

Glu Ser Thr Thr Thr Glu Thr Leu Val Met Gly Val Ala Pro Val Lys
        35                  40                  45

Ala Gln Phe Glu Ser Ala Glu Met Gly Val Pro Ala Glu Asn Asp Gly
    50                  55                  60

Cys Lys Cys Gly Ala Asn Cys Thr Cys Asn Pro Cys Thr Cys Lys
65                  70                  75

<210> SEQ ID NO 17
<211> LENGTH: 4942
<212> TYPE: DNA

<213> ORGANISM: Artificial sequence
<220> FEATURE:
<223> OTHER INFORMATION: plasmid QC371

<400> SEQUENCE: 17

| | | | | | |
|---|---|---|---|---|---|
| catggcccac | agcaagcacg | gcctgaagga | ggagatgacc | atgaagtacc | acatggaggg | 60 |
| ctgcgtgaac | ggccacaagt | tcgtgatcac | cggcgagggc | atcggctacc | ccttcaaggg | 120 |
| caagcagacc | atcaacctgt | gcgtgatcga | gggcggcccc | ctgcccttca | gcgaggacat | 180 |
| cctgagcgcc | ggcttcaagt | acggcgaccg | gatcttcacc | gagtaccccc | aggacatcgt | 240 |
| ggactacttc | aagaacagct | gccccgccgg | ctacacctgg | ggccggagct | tcctgttcga | 300 |
| ggacggcgcc | gtgtgcatct | gtaacgtgga | catcaccgtg | agcgtgaagg | agaactgcat | 360 |
| ctaccacaag | agcatcttca | acggcgtgaa | cttccccgcc | gacggccccg | tgatgaagaa | 420 |
| gatgaccacc | aactgggagg | ccagctgcga | gaagatcatg | cccgtgccta | gcagggcat | 480 |
| cctgaagggc | gacgtgagca | tgtacctgct | gctgaaggac | ggcggccggt | accggtgcca | 540 |
| gttcgacacc | gtgtacaagg | ccaagagcgt | gcccagcaag | atgcccgagt | ggcacttcat | 600 |
| ccagcacaag | ctgctgcggg | aggaccggag | cgacgccaag | aaccagaagt | ggcagctgac | 660 |
| cgagcacgcc | atcgccttcc | ccagcgccct | ggcctgagag | ctcgaatttc | cccgatcgtt | 720 |
| caaacatttg | gcaataaagt | ttcttaagat | tgaatcctgt | tgccggtctt | gcgatgatta | 780 |
| tcatataatt | tctgttgaat | tacgttaagc | atgtaataat | taacatgtaa | tgcatgacgt | 840 |
| tatttatgag | atgggttttt | atgattagag | tcccgcaatt | atacatttaa | tacgcgatag | 900 |
| aaaacaaaat | atagcgcgca | aactaggata | aattatcgcg | cgcggtgtca | tctatgttac | 960 |
| tagatcggga | attctagtgg | ccggcccagc | tgatatccat | cacactggcg | gccgcactcg | 1020 |
| actgaattgg | ttccggcgcc | agcctgcttt | tttgtacaaa | gttggcatta | taaaaaagca | 1080 |
| ttgcttatca | atttgttgca | acgaacaggt | cactatcagt | caaaataaaa | tcattatttg | 1140 |
| gggcccgagc | ttaagtaact | aactaacagg | aagagtttgt | agaaacgcaa | aaaggccatc | 1200 |
| cgtcaggatg | gccttctgct | tagtttgatg | cctggcagtt | tatggcgggc | gtcctgcccg | 1260 |
| ccaccctccg | ggccgttgct | tcacaacgtt | caaatccgct | cccggcggat | ttgtcctact | 1320 |
| caggagagcg | ttcaccgaca | acaacagat | aaaacgaaag | gcccagtctt | ccgactgagc | 1380 |
| cttttcgtttt | atttgatgcc | tggcagttcc | ctactctcgc | ttagtagtta | gacgtccccg | 1440 |
| agatccatgc | tagcggtaat | acggttatcc | acagaatcag | gggataacgc | aggaaagaac | 1500 |
| atgtgagcaa | aaggccagca | aaaggccagg | aaccgtaaaa | aggccgcgtt | gctggcgttt | 1560 |
| ttccataggc | tccgcccccc | tgacgagcat | cacaaaaatc | gacgctcaag | tcagaggtgg | 1620 |
| cgaaacccga | caggactata | aagataccag | gcgtttcccc | ctggaagctc | cctcgtgcgc | 1680 |
| tctcctgttc | cgaccctgcc | gcttaccgga | tacctgtccg | cctttctccc | ttcgggaagc | 1740 |
| gtggcgcttt | ctcatagctc | acgctgtagg | tatctcagtt | cggtgtaggt | cgttcgctcc | 1800 |
| aagctgggct | gtgtgcacga | accccccgtt | cagcccgacc | gctgcgcctt | atccggtaac | 1860 |
| tatcgtcttg | agtccaaccc | ggtaagacac | gacttatcgc | cactggcagc | agccactggt | 1920 |
| aacaggatta | gcagagcgag | gtatgtaggc | ggtgctacag | agttcttgaa | gtggtggcct | 1980 |
| aactacggct | acactagaag | aacagtattt | ggtatctgcg | ctctgctgaa | gccagttacc | 2040 |
| ttcggaaaaa | gagttggtag | ctcttgatcc | ggcaaacaaa | ccaccgctgg | tagcggtggt | 2100 |
| ttttttgttt | gcaagcagca | gattacgcgc | agaaaaaaag | gatctcaaga | agatcctttg | 2160 |
| atcttttcta | cggggtctga | cgctcagtgg | aacgggccc | aatctgaata | atgttacaac | 2220 |

```
caattaacca attctgatta gaaaaactca tcgagcatca aatgaaactg caatttattc    2280
atatcaggat tatcaatacc atattttga aaaagccgtt tctgtaatga aggagaaaac    2340
tcaccgaggc agttccatag gatggcaaga tcctggtatc ggtctgcgat tccgactcgt    2400
ccaacatcaa tacaacctat taatttcccc tcgtcaaaaa taaggttatc aagtgagaaa    2460
tcaccatgag tgacgactga atccggtgag aatggcaaaa gtttatgcat ttctttccag    2520
acttgttcaa caggccagcc attacgctcg tcatcaaaat cactcgcatc aaccaaaccg    2580
ttattcattc gtgattgcgc ctgagcgaga cgaaatacgc gatcgctgtt aaaaggacaa    2640
ttacaaacag gaatcgaatg caaccggcgc aggaacactg ccagcgcatc aacaatattt    2700
tcacctgaat caggatattc ttctaatacc tggaatgctg ttttccggg gatcgcagtg    2760 gtgagtaacc atgcatcatc aggagtacgg ataaaatgct tgatggtcgg aagaggcata    2820
aattccgtca gccagtttag tctgaccatc tcatctgtaa catcattggc aacgctacct    2880
ttgccatgtt tcagaaacaa ctctggcgca tcgggcttcc catacaagcg atagattgtc    2940
gcacctgatt gcccgacatt atcgcgagcc catttatacc catataaatc agcatccatg    3000
ttggaattta atcgcggcct cgacgttttc cgttgaatat ggctcataac cccccttgta    3060
ttactgttta tgtaagcaga cagttttatt gttcatgatg atatatttt atcttgtgca    3120 atgtaacatc agagattttg agacacgggc cagagctgca gctggatggc aaataatgat    3180
tttattttga ctgatagtga cctgttcgtt gcaacaaatt gataagcaat gcttcttat    3240 aatgccaact tgtacaaga aagctgggtc tagatatctc gacccgggtg aaatggaacg    3300
tgtgtgatgg gtacaagttg cttgtggtgt atcatgtatg agtataaaat ttagctcaaa    3360
taacttatca ttgaacggac ttagttatac tttttttt ttttatcttt ctaatacata    3420
tatttcgttg ttataaaagt agaaatgttc gatttctgta aaattatcgt tgattttct    3480 tccacgtaaa ataaaattaa aatatgttat attttagaa cataacaaga ttcgtgtaaa    3540
tttaaatttg tgagaatttc taaaaatcaa ttaaaaatca tcacaaatta cagaaaaacc    3600
atcataaatt atagaataaa aataaatca aatacaaatt atgatggttt ttaacctcaa    3660
acttaaatct taaatatatt tttaaccttt aaagatatga ttttttggag ggcaaaaata    3720
tgacctttct tcaaagtagt ccatttgttt gtatttatta ttaattgtaa atattatttt    3780
tagcaccaaa atatcttggc ataaaattaa aacacacatt ttttttctaa ggtaaacatt    3840
aaaaaaagaa ctcattccaa aaaagtaaca tgtttcaaaa aatccaaaaa catttaaatt    3900
ttaaaataat tctagtaata gtatttatat ttaatattaa aactcacaaa taatgagat    3960 tgcccgtttt atataaaatt gggatgagta atatgtatg atacaattat ataaggacaa    4020
ttaagtataa ttatgtgtgc atgttaaagt tgatttaatt aaataagatg cgtaaattat    4080 tataacttt tttaacatt tatacttgct aacacaccc atattcacat gataatagga    4140
ggcatctcta atgagttgat attttttacac gagagtgatg agtaagtttg aattatgcaa    4200
tcataaatag taaaatttaa caatcaatat ttatttacct tatttgtaag tgaaaaaaaa    4260
tatttgtata tatattataa tttaaagtat aaatgaattt aaatgaaata ttaggctgtg    4320
aaattaatca taagattcac aaataagaat ctagatgaat taattaatac ccatagtgaa    4380
aaatagtggt ctcattaaga aaaaaattga aaactcaagt ttatgttgtg cacttttgct    4440
atgtaagaga gaggaaagga ttaaaatgaa atgagcaagc tttataaaaa aatataaatt    4500
taaaaaaaaa aaaaaaaaaa aagcacgagg tagagtagaa tgattgcatg agtggcacat    4560
ggtgacaaat tcgagacaga tattttcaca cctttccatc acatcaactc tccccgttg    4620
```

| | |
|---|---|
| atcatcattt aatatctcat ccaacggcaa acaaacgtac attttagaac ataccagaaa | 4680 |
| atccctctct ctcatcaatc cacccaagtg atgaaaacga cgtcgacgtg ggagaagatc | 4740 |
| cgcaaacgga ttagacgcgt cgtcagattt cgacacgtgt acggtggatg tttcggactc | 4800 |
| tctcccctca accgctttat aaattggggt cgtggcttcg ccttgaaact cgttctagtg | 4860 |
| tatgtgattg ttgtgactcg ttcttcttcg tcgttatctt cttctttgt tgtttgtgtg | 4920 |
| tttgttttt ctctcacctg ac | 4942 |

<210> SEQ ID NO 18
<211> LENGTH: 9467
<212> TYPE: DNA
<213> ORGANISM: Artificial sequence
<220> FEATURE:
<223> OTHER INFORMATION: plasmid QC383

<400> SEQUENCE: 18

| | |
|---|---|
| tttgtacaaa cttgttgatg gggttaacat atcataactt cgtataatgt atgctatacg | 60 |
| aagttatagg cctggatctt cgaggtcgag cggccgcaga tttaggtgac actatagaat | 120 |
| atgcatcact agtaagcttt gctctagatc aaactcacat ccaaacataa catgatatc | 180 |
| ttccttacca atcatactaa ttattttggg ttaaatatta atcattattt ttaagatatt | 240 |
| aattaagaaa ttaaaagatt ttttaaaaaa atgtataaaa ttatattatt catgattttt | 300 |
| catacatttg attttgataa taaatatatt tttttaatt tcttaaaaaa tgttgcaaga | 360 |
| cacttattag acatagtctt gttctgttta caaaagcatt catcatttaa tacattaaaa | 420 |
| aatatttaat actaacagta gaatcttctt gtgagtggtg tgggagtagg caacctggca | 480 |
| ttgaaacgag agaagagag tcagaaccag aagacaaata aaagtatgc aacaaacaaa | 540 |
| tcaaaatcaa agggcaaagg ctggggttgg ctcaattggt tgctacattc aattttcaac | 600 |
| tcagtcaacg gttgagattc actctgactt ccccaatcta agccgcggat gcaaacggtt | 660 |
| gaatctaacc cacaatccaa tctcgttact tagggctttt ccgtcatta actcacccct | 720 |
| gccacccggt ttccctataa attggaactc aatgctcccc tctaaactcg tatcgcttca | 780 |
| gagttgagac caagacacac tcgttcatat atctctctgc tcttctcttc tcttctacct | 840 |
| ctcaaggtac ttttcttctc cctctaccaa atcctagatt ccgtggttca atttcggatc | 900 |
| ttgcacttct ggtttgcttt gccttgcttt ttcctcaact gggtccatct aggatccatg | 960 |
| tgaaactcta ctctttcttt aatatctgcg gaatacgcgt ttgactttca gatctagtcg | 1020 |
| aaatcatttc ataattgcct ttctttcttt tagcttatga gaaataaaat cactttttt | 1080 |
| ttatttcaaa ataaaccttg ggccttgtgc tgactgagat ggggtttggt gattacagaa | 1140 |
| ttttagcgaa ttttgtaatt gtacttgttt gtctgtagtt ttgttttgtt ttcttgtttc | 1200 |
| tcatacattc cttaggcttc aattttattc gagtataggt cacaatagga attcaaactt | 1260 |
| tgagcagggg aattaatccc ttccttcaaa tccagtttgt ttgtatatat gtttaaaaaa | 1320 |
| tgaaactttt gctttaaatt ctattataac tttttttatg gctgaaattt ttgcatgtgt | 1380 |
| ctttgctctc tgttgtaaat ttactgttta ggtactaact ctaggcttgt tgtgcagttt | 1440 |
| ttgaagtata accatgccac acaacacaat ggcggccacc gcttccagaa ccacccgatt | 1500 |
| ctcttcttcc tcttcacacc ccaccttccc caaacgcatt actagatcca ccctccctct | 1560 |
| ctctcatcaa accctcacca aacccaacca cgctctcaaa atcaaatgtt ccatctccaa | 1620 |
| acccccacg cgcggcgccct tcaccaagga agcgccgacc acggagccct tcgtgtcacg | 1680 |
| gttcgcctcc ggcgaacctc gcaagggcgc ggacatcctg gtggaggcgc tggagaggca | 1740 |

```
gggcgtgacg acggtgttcg cgtacccggg cggtgcgtcg atggagatcc accaggcgct    1800
cacgcgctcc gccgccatcc gcaacgtgct cccgcgccac gagcagggcg gcgtcttcgc    1860
cgccgaaggc tacgcgcgtt cctccggcct ccccggcgtc tgcattgcca cctccggccc    1920
cggcgccacc aacctcgtga gcggcctcgc cgacgcttta atggacagcg tcccagtcgt    1980
cgccatcacc ggccaggtcg cccgccggat gatcggcacc gacgccttcc aagaaacccc    2040
gatcgtggag gtgagcagat ccatcacgaa gcacaactac ctcatcctcg acgtcgacga    2100
catcccccgc gtcgtcgccg aggctttctt cgtcgccacc tccggccgcc ccggtccggt    2160
cctcatcgac attcccaaag acgttcagca gcaactcgcc gtgcctaatt gggacgagcc    2220
cgttaacctc cccggttacc tcgccaggct gcccaggccc cccgccgagg cccaattgga    2280
acacattgtc agactcatca tggaggccca aaagcccgtt ctctacgtcg gcggtggcag    2340
tttgaattcc agtgctgaat tgaggcgctt tgttgaactc actggtattc ccgttgctag    2400
cactttaatg ggtcttggaa cttttcctat tggtgatgaa tattcccttc agatgctggg    2460
tatgcatggt actgtttatg ctaactatgc tgttgacaat agtgatttgt tgcttgcctt    2520
tggggtaagg tttgatgacc gtgttactgg gaagcttgag gcttttgcta gtagggctaa    2580
gattgttcac attgatattg attctgccga gattgggaag aacaagcagg cgcacgtgtc    2640
ggtttgcgcg gatttgaagt tggccttgaa gggaattaat atgattttgg aggagaaagg    2700
agtggagggt aagtttgatc ttggaggttg gagagaagag attaatgtgc agaaacacaa    2760
gtttccattg ggttacaaga cattccagga cgcgatttct ccgcagcatg ctatcgaggt    2820
tcttgatgag ttgactaatg gagatgctat tgttagtact ggggttgggc agcatcaaat    2880
gtgggctgcg cagttttaca agtacaagag accgaggcag tggttgacct caggggggtct    2940 tggagccatg ggttttggat tgcctgcggc tattggtgct gctgttgcta accctggggc    3000
tgttgtggtt gacattgatg gggatggtag tttcatcatg aatgttcagg agttggccac    3060
tataagagtg gagaatctcc cagttaagat attgttgttg aacaatcagc atttgggtat    3120
ggtggttcag ttggaggata ggttctacaa gtccaataga gctcacacct atcttggaga    3180
tccgtctagc gagagcgaga tattcccaaa catgctcaag tttgctgatg cttgtgggat    3240
accggcagcg cgagtgacga agaaggaaga gcttagagcg gcaattcaga gaatgttgga    3300
cacccctggc ccctaccttc ttgatgtcat tgtgccccat caggagcatg tgttgccgat    3360
gattcccagt aatggatcct tcaaggatgt gataactgag ggtgatggta gaacgaggta    3420
ctgattgcct agaccaaatg ttccttgatg cttgttttgt acaatatata taagataatg    3480
ctgtcctagt tgcaggattt ggcctgtggt gagcatcata gtctgtagta gttttggtag    3540
caagacattt tattttcctt ttatttaact tactacatgc agtagcatct atctatctct    3600
gtagtctgat atctcctgtt gtctgtattg tgccgttgga tttttttgctg tagtgagact    3660 gaaaatgatg tgctagtaat aatatttctg ttagaaatct aagtagagaa tctgttgaag    3720
aagtcaaaag ctaatggaat caggttacat attcaatgtt tttcttttt tagcggttgg    3780 tagacgtgta gattcaactt ctcttggagc tcacctaggc aatcagtaaa atgcatattc    3840
cttttttaac ttgccatttta tttactttta gtggaaattg tgaccaattt gttcatgtag    3900
aacggatttg gaccattgcg tccacaaaac gtctcttttg ctcgatcttc acaaagcgat    3960
accgaaatcc agagatagtt ttcaaaagtc agaaatggca aagttataaa tagtaaaaca    4020
gaatagatgc tgtaatcgac ttcaataaca agtggcatca cgtttctagt tctagaccca    4080
tcagatcgaa ttaacatatc ataacttcgt ataatgtatg ctatacgaag ttataggcct    4140
```

```
ggatccacta gttctagagc ggccgctcga gggggggccc ggtaccggcg cgccgttcta   4200
tagtgtcacc taaatcgtat gtgtatgata cataaggtta tgtattaatt gtagccgcgt   4260
tctaacgaca atatgtccat atggtgcact ctcagtacaa tctgctctga tgccgcatag   4320
ttaagccagc cccgacaccc gccaacaccc gctgacgcgc cctgacgggc ttgtctgctc   4380
ccggcatccg cttacagaca agctgtgacc gtctccggga gctgcatgtg tcagaggttt   4440
tcaccgtcat caccgaaacg cgcgagacga aagggcctcg tgatacgcct attttatag    4500 gttaatgtca tgaccaaaat cccttaacgt gagttttcgt tccactgagc gtcagacccc   4560
gtagaaaaga tcaaaggatc ttcttgagat cctttttttc tgcgcgtaat ctgctgcttg   4620
caaacaaaaa aaccaccgct accagcggtg gtttgtttgc cggatcaaga gctaccaact   4680
ctttttccga aggtaactgg cttcagcaga gcgcagatac caaatactgt ccttctagtg   4740
tagccgtagt taggccacca cttcaagaac tctgtagcac cgcctacata cctcgctctg   4800
ctaatcctgt taccagtggc tgctgccagt ggcgataagt cgtgtcttac cgggttggac   4860
tcaagacgat agttaccgga taaggcgcag cggtcgggct gaacggggg ttcgtgcaca    4920 cagcccagct tggagcgaac gacctacacc gaactgagat acctacagcg tgagcattga   4980
gaaagcgcca cgcttcccga agggagaaag gcggacaggt atccggtaag cggcagggtc   5040
ggaacaggag agcgcacgag ggagcttcca ggggaaacg cctggtatct ttatagtcct    5100
gtcgggtttc gccacctctg acttgagcgt cgatttttgt gatgctcgtc agggggcgg    5160 agcctatgga aaacgccag caacgcggcc ttttacggt tcctggcctt ttgctggcct     5220
tttgctcaca tgttctttcc tgcgttatcc cctgattctg tggataaccg tattaccgcc   5280
tttgagtgag ctgataccgc tcgccgcagc cgaacgaccg agcgcagcga gtcagtgagc   5340
gaggaagcgg aagagcgccc aatacgcaaa ccgcctctcc ccgcgcgttg gccgattcat   5400
taatgcaggt tgatcagatc tcgatcccgc gaaattaata cgactcacta tagggagacc   5460
acaacggttt ccctctagaa ataattttgt ttaactttaa gaaggagata tacccatgga   5520
aaagcctgaa ctcaccgcga cgtctgtcga agtttctg atcgaaaagt tcgacagcgt     5580
ctccgacctg atgcagctct cggagggcga agaatctcgt gctttcagct tcgatgtagg   5640
agggcgtgga tatgtcctgc gggtaaatag ctgcgccgat ggtttctaca agatcgtta    5700 tgtttatcgg cactttgcat cggccgcgct cccgattccg gaagtgcttg acattgggga   5760
attcagcgag agcctgacct attgcatctc ccgccgtgca cagggtgtca cgttgcaaga   5820
cctgcctgaa accgaactgc ccgctgttct gcagccggtc gcggaggcta tggatgcgat   5880
cgctgcggcc gatcttagcc agacgagcgg gttcggccca ttcggaccgc aaggaatcgg   5940
tcaatacact acatggcgtg atttcatatg cgcgattgct gatccccatg tgtatcactg   6000
gcaaactgtg atggacgaca ccgtcagtgc gtccgtcgcg caggctctcg atgagctgat   6060
gctttgggcc gaggactgcc ccgaagtccg gcacctcgtg cacgcggatt tcggctccaa   6120
caatgtcctg acggacaatg gccgcataac agcggtcatt gactggagcg aggcgatgtt   6180
cggggattcc caatacgagg tcgccaacat cttcttctgg aggccgtggt tggcttgtat   6240
ggagcagcag acgcgctact cgagcggag gcatccggag cttgcaggat cgccgcggct    6300
ccgggcgtat atgctccgca ttggtcttga ccaactctat cagagcttgg ttgacggcaa   6360
tttcgatgat gcagcttggg cgcagggtcg atgcgacgca atcgtccgat ccggagccgg   6420
gactgtcggg cgtacacaaa tcgcccgcag aagcgcggcc gtctgaccg atggctgtgt    6480 agaagtactc gccgatagtg gaaaccgacg ccccagcact cgtccgaggg caaaggaata   6540
```

```
gtgaggtaca gcttggatcg atccggctgc taacaaagcc cgaaaggaag ctgagttggc    6600
tgctgccacc gctgagcaat aactagcata acccccttggg gcctctaaac gggtcttgag    6660
gggttttttg ctgaaaggag gaactatatc cggatgatcg ggcgcgccgg tacccatcaa    6720
ccactttgta caagaaagct gggtctagat atctcgaccc gggtgaaatg gaacgtgtgt    6780
gatgggtaca agttgcttgt ggtgtatcat gtatgagtat aaaatttagc tcaaataact    6840
tatcattgaa cggacttagt tatacttttt ttttttttta tctttctaat acatatattt    6900
cgttgttata aaagtagaaa tgttcgattt ctgtaaaatt atcgttgatt tttcttccac    6960
gtaaaataaa attaaaatat gttatatttt tagaacataa caagattcgt gtaaatttaa    7020
atttgtgaga atttctaaaa atcaattaaa aatcatcaca aattacagaa aaaccatcat    7080
aaattataga ataaaaataa atacaaatac aaattatgat ggttttttaac ctcaaactta    7140 aatcttaaat atattttttaa cctttaaaga tatgattttt tggagggcaa aaatatgacc    7200
tttcttcaaa gtagtccatt tgtttgtatt tattattaat tgtaaatatt atttttagca    7260
ccaaaatatc ttggcataaa attaaaacac acatttttttt tctaaggtaa acattaaaaa    7320
aagaactcat tccaaaaaag taacatgttt caaaaaatcc aaaaacattt aaatttttaaa    7380 ataattctag taatagtatt tatatttaat attaaaactc acaaataaat gagattgccc    7440
gttttatata aaatttgggat gagtaaatat gtatgataca attatataag gacaattaag    7500
tataattatg tgtgcatgtt aaagttgatt taattaaata agatgcgtaa attattataa    7560 cttttttttta acatttatac ttgctaacac accccatatt cacatgataa taggaggcat    7620
ctctaatgag ttgatatttt tacacgagag tgatgagtaa gtttgaatta tgcaatcata    7680
aatagtaaaa tttaacaatc aatatttatt taccttattt gtaagtgaaa aaaaatatttt    7740 gtatatatat tataatttaa agtataaatg aatttaaatg aaatattagg ctgtgaaatt    7800
aatcataaga ttcacaaata agaatctaga tgaattaatt aatacccata gtgaaaaata    7860
gtggtctcat taagaaaaaa attgaaaact caagtttatg ttgtgcactt ttgctatgta    7920
agagagagga aaggattaaa atgaaatgag caagctttat aaaaaaatat aaattttaaaa    7980 aaaaaaaaaa aaaaaaagca cgaggtagag tagaatgatt gcatgagtgg cacatggtga    8040
caaattcgag acagatattt tcacaccttt ccatcacatc aactctcccc cgttgatcat    8100
catttaatat ctcatccaac ggcaaacaaa cgtacatttt agaacatacc agaaaatccc    8160
tctctctcat caatccaccc aagtgatgaa aacgacgtcg acgtgggaga agatccgcaa    8220
acggattaga cgcgtcgtca gatttcgaca cgtgtacggt ggatgtttcg gactctctcc    8280
cctcaaccgc tttataaatt ggggtcgtgg cttcgccttg aaactcgttc tagtgtatgt    8340
gattgttgtg actcgttctt cttcgtcgtt atcttcttct tttgttgttt gtgtgtttgt    8400 ttttctctc acctgaccat ggcccacagc aagcacggcc tgaaggagga gatgaccatg    8460
aagtaccaca tggagggctg cgtgaacggc cacaagttcg tgatcaccgg cgagggcatc    8520
ggctacccct tcaagggcaa gcagaccatc aacctgtgcg tgatcgaggg cggccccctg    8580
cccttcagcg aggacatcct gagcgccggc ttcaagtacg gcgaccggat cttcaccgag    8640
tacccccagg acatcgtgga ctacttcaag aacagctgcc ccgccggcta cacctggggc    8700
cggagcttcc tgttcgagga cggcgccgtg tgcatctgta acgtggacat caccgtgagc    8760
gtgaaggaga actgcatcta ccacaagagc atcttcaacg gcgtgaactt ccccgccgac    8820
ggccccgtga tgaagaagat gaccaccaac tgggaggcca gctgcgagaa gatcatgccc    8880
gtgcctaagc agggcatcct gaagggcgac gtgagcatgt acctgctgct gaaggacggc    8940
```

```
ggccggtacc ggtgccagtt cgacaccgtg tacaaggcca agagcgtgcc cagcaagatg    9000
cccgagtggc acttcatcca gcacaagctg ctgcgggagg accggagcga cgccaagaac    9060
cagaagtggc agctgaccga gcacgccatc gccttcccca gcgccctggc ctgagagctc    9120
gaatttcccc gatcgttcaa acatttggca ataaagtttc ttaagattga atcctgttgc    9180
cggtcttgcg atgattatca tataatttct gttgaattac gttaagcatg taataattaa    9240
catgtaatgc atgacgttat ttatgagatg gttttttatg attagagtcc cgcaattata    9300
catttaatac gcgatagaaa acaaaatata gcgcgcaaac taggataaat tatcgcgcgc    9360
ggtgtcatct atgttactag atcgggaatt ctagtggccg cccagctga tatccatcac     9420 actgcggcc gcactcgact gaattggttc cggcgccagc ctgcttt                   9467

<210> SEQ ID NO 19
<211> LENGTH: 4913
<212> TYPE: DNA
<213> ORGANISM: Artificial sequence
<220> FEATURE:
<223> OTHER INFORMATION: plasmid QC371-1Y

<400> SEQUENCE: 19
cttgtacaaa gtggttgatg ggatccatgg cccacagcaa gcacggcctg aaggaggaga      60
tgaccatgaa gtaccacatg gagggctgcg tgaacggcca caagttcgtg atcaccggcg     120
agggcatcgg ctaccccttc aagggcaagc agaccatcaa cctgtgcgtg atcgagggcg     180
gccccctgcc cttcagcgag gacatcctga gcgccggctt caagtacggc gaccggatct     240
tcaccgagta cccccaggac atcgtggact acttcaagaa cagctgcccc gccggctaca     300
cctggggccg gagcttcctg ttcgaggacg gcgccgtgtg catctgtaac gtggacatca     360
ccgtgagcgt gaaggagaac tgcatctacc acaagagcat cttcaacggc gtgaacttcc     420
ccgccgacgg ccccgtgatg aagaagatga ccaccaactg ggaggccagc tgcgagaaga     480
tcatgcccgt gcctaagcag ggcatcctga agggcgacgt gagcatgtac ctgctgctga     540
aggacggcgg ccggtaccgg tgccagttcg acaccgtgta caaggccaag agcgtgccca     600
gcaagatgcc cgagtggcac ttcatccagc acaagctgct gcgggaggac cggagcgacg     660
ccaagaacca gaagtggcag ctgaccgagc acgccatcgc cttccccagc gccctggcct     720
gagagctcga atttccccga tcgttcaaac atttggcaat aaagtttctt aagattgaat     780
cctgttgccg gtcttgcgat gattatcata taatttctgt tgaattacgt taagcatgta     840
ataattaaca tgtaatgcat gacgttattt atgagatggg ttttttatgat tagagtcccg    900 caattataca tttaatacgc gatagaaaac aaaatatagc gcgcaaacta ggataaatta     960 tcgcgcgcg tgtcatctat gttactagat cgggaattct agtggccggc cagctgata     1020 tccatcacac tggcggccgc tcgagttcta tagtgtcacc taaatcgtat gtgtatgata    1080
cataaggtta tgtattaatt gtagccgcgt tctaacgaca atatgtccat atggtgcact    1140
ctcagtacaa tctgctctga tgccgcatag ttaagccagc ccgacaccc gccaacaccc     1200 gctgacgcgc cctgacgggc ttgtctgctc ccggcatccg cttacagaca agctgtgacc    1260
gtctccggga gctgcatgtg tcagaggttt tcaccgtcat caccgaaacg cgcgagacga    1320
aagggcctcg tgatacgcct atttttatag gttaatgtca tgaccaaaat cccttaacgt    1380
gagttttcgt tccactgagc gtcagacccc gtagaaaaga tcaaaggatc ttcttgagat    1440 ccttttttc tgcgcgtaat ctgctgcttg caaacaaaaa aaccaccgct accagcggtg     1500
gtttgtttgc cggatcaaga gctaccaact ctttttccga aggtaactgg cttcagcaga    1560
```

```
gcgcagatac caaatactgt ccttctagtg tagccgtagt taggccacca cttcaagaac    1620
tctgtagcac cgcctacata cctcgctctg ctaatcctgt taccagtggc tgctgccagt    1680
ggcgataagt cgtgtcttac cgggttggac tcaagacgat agttaccgga taaggcgcag    1740
cggtcgggct gaacgggggg ttcgtgcaca cagcccagct tggagcgaac gacctacacc    1800
gaactgagat acctacagcg tgagcattga aaagcgcca cgcttcccga agggagaaag     1860
gcggacaggt atccggtaag cggcagggtc ggaacaggag agcgcacgag ggagcttcca    1920
gggggaaacg cctggtatct ttatagtcct gtcgggtttc gccacctctg acttgagcgt    1980
cgatttttgt gatgctcgtc agggggggcgg agcctatgga aaaacgccag caacgcggcc    2040
tttttacggt tcctggcctt ttgctggcct tttgctcaca tgttctttcc tgcgttatcc    2100
cctgattctg tggataaccg tattaccgcc tttgagtgag ctgataccgc tcgccgcagc    2160
cgaacgaccg agcgcagcga gtcagtgagc gaggaagcgg aagagcgccc aatacgcaaa    2220
ccgcctctcc ccgcgcgttg ccgattcat taatgcaggt tgatcagatc tcgatcccgc     2280
gaaattaata cgactcacta tagggagacc acaacggttt ccctctagaa ataattttgt    2340
ttaactttaa gaaggagata tacccatgga aaagcctgaa ctcaccgcga cgtctgtcga    2400
gaagtttctg atcgaaaagt tcgacagcgt ctccgacctg atgcagctct cggagggcga    2460
agaatctcgt gctttcagct tcgatgtagg agggcgtgga tatgtcctgc gggtaaatag    2520
ctgcgccgat ggtttctaca agatcgtta tgtttatcgg cactttgcat cggccgcgct    2580
cccgattccg gaagtgcttg acattgggga attcagcgag agcctgacct attgcatctc    2640
ccgccgtgca cagggtgtca cgttgcaaga cctgcctgaa accgaactgc cgctgttct     2700 gcagccggtc gcggaggcta tggatgcgat cgctgcggcc gatcttagcc agacgagcgg    2760
gttcggccca ttcggaccgc aaggaatcgg tcaatacact acatggcgtg atttcatatg    2820
cgcgattgct gatccccatg tgtatcactg gcaaactgtg atggacgaca ccgtcagtgc    2880
gtccgtcgcg caggctctcg atgagctgat gctttgggcc gaggactgcc ccgaagtccg    2940
gcacctcgtg cacgcggatt tcggctccaa caatgtcctg acggacaatg gccgcataac    3000
agcggtcatt gactggagcg aggcgatgtt cggggattcc caatacgagg tcgccaacat    3060
cttcttctgg aggccgtggt tggcttgtat ggagcagcag acgcgctact tcgagcggag    3120
gcatccggag cttgcaggat cgccgcggct ccgggcgtat atgctccgca ttggtcttga    3180
ccaactctat cagagcttgg ttgacggcaa tttcgatgat gcagcttggg cgcagggtcg    3240
atgcgacgca atcgtccgat ccggagccgg gactgtcggg cgtacacaaa tcgcccgcag    3300
aagcgcggcc gtctggaccg atggctgtgt agaagtactc gccgatagtg aaaccgacg     3360 ccccagcact cgtccgaggg caaggaata gtgaggtaca gcttggatcg atccggctgc     3420
taacaaagcc cgaaaggaag ctgagttggc tgctgccacc gctgagcaat aactagcata    3480
accccttggg gcctctaaac gggtcttgag ggtttttttg ctgaaaggag gaactatatc    3540
cggatgatcg tcgaggcctc acgtgttaac aagcttgcat gcctgcaggt ttatcaacaa    3600
gtttgtacaa aaaagcaggc tccgaattcg ccccttttaaa gatatgattt tttgagggc    3660 aaaaatatga cctttcttca aagtagtcca tttgtttgta tttattatta attgtaaata    3720 ttattttttag caccaaaata tcttggcata aaattaaaac acacattttt tttctaaggt    3780
aaacattaaa aaagaactc attccaaaaa agtaacatgt ttcaaaaaat ccaaaaacat     3840 ttaaattttta aaataattct agtaatagta tttatattta atattaaaac tcacaaataa    3900
atgagattgc ccgttttata taaaattggg atgagtaaat atgtatgata caattatata    3960
```

-continued

```
aggacaatta agtataatta tgtgtgcatg ttaaagttga tttaattaaa taagatgcgt    4020
aaattattat aacttttttt taacatttat acttgctaac acaccccata ttcacatgat    4080
aataggaggc atctctaatg agttgatatt tttacacgag agtgatgagt aagtttgaat    4140
tatgcaatca taaatagtaa aatttaacaa tcaatattta tttacccat ttgtaagtga     4200 aaaaaaatat ttgtatatat attataattt aaagtataaa tgaatttaaa tgaaatatta    4260
ggctgtgaaa ttaatcataa gattcacaaa taagaatcta gatgaattaa ttaataccca    4320
tagtgaaaaa tagtggtctc attaagaaaa aaattgaaaa ctcaagttta tgttgtgcac    4380
ttttgctatg taagagagag gaaaggatta aaatgaaatg agcaagcttt ataaaaaaat    4440
ataaatttaa aaaaaaaaaa aaaaaaaaag cacgaggtag agtagaatga ttgcatgagt    4500
ggcacatggt gacaaaattcg agacagatat tttcacacct ttccatcaca tcaactctcc   4560
cccgttgatc atcatttaat atctcatcca acggcaaaca aacgtacatt ttagaacata    4620
ccagaaaatc cctctctctc atcaatccac ccaagtgatg aaaacgacgt cgacgtggga    4680
gaagatccgc aaacggatta gacgcgtcgt cagatttcga cacgtgtacg gtggatgttt    4740
cggactctct cccctcaacc gctttataaa ttggggtcgt ggcttcgcct tgaaactcgt    4800
tctagtgtat gtgattgttg tgactcgttc ttcttcgtcg ttatcttctt cttttgttgt    4860
ttgtgtgttt gtttttttctc tcacctgacc aagggcgaat tcgacccagc ttt          4913
```

<210> SEQ ID NO 20
<211> LENGTH: 26
<212> TYPE: DNA
<213> ORGANISM: Artificial seqeunce
<220> FEATURE:
<223> OTHER INFORMATION: Sams-L primer

<400> SEQUENCE: 20
gaccaagaca cactcgttca tatatc                                          26

<210> SEQ ID NO 21
<211> LENGTH: 25
<212> TYPE: DNA
<213> ORGANISM: Artificial seqeunce
<220> FEATURE:
<223> OTHER INFORMATION: Sams-L2 primer

<400> SEQUENCE: 21
tctgctgctc aatgtttaca aggac                                           25

<210> SEQ ID NO 22
<211> LENGTH: 20
<212> TYPE: DNA
<213> ORGANISM: Artificial seqeunce
<220> FEATURE:
<223> OTHER INFORMATION: PSO333209 sense primer

<400> SEQUENCE: 22
tcatgggagt ggcaccagtt                                                 20

<210> SEQ ID NO 23
<211> LENGTH: 19
<212> TYPE: DNA
<213> ORGANISM: Artificial seqeunce
<220> FEATURE:
<223> OTHER INFORMATION: PSO333209 antisense primer

<400> SEQUENCE: 23
tcgttctcag cgggaacac                                                  19

-continued

```
<210> SEQ ID NO 24
<211> LENGTH: 24
<212> TYPE: DNA
<213> ORGANISM: Artificial seqeunce
<220> FEATURE:
<223> OTHER INFORMATION: ATPS sense primer

<400> SEQUENCE: 24
catgattggg agaaacctta agct                                              24

<210> SEQ ID NO 25
<211> LENGTH: 20
<212> TYPE: DNA
<213> ORGANISM: Artificial seqeunce
<220> FEATURE:
<223> OTHER INFORMATION: ATPS antisense primer

<400> SEQUENCE: 25
agattgggcc agaggatcct                                                   20

<210> SEQ ID NO 26
<211> LENGTH: 21
<212> TYPE: DNA
<213> ORGANISM: Artificial seqeunce
<220> FEATURE:
<223> OTHER INFORMATION: PSO333209 sense primer, PSO333209JK-S

<400> SEQUENCE: 26
gtcaaccacc accgagacct t                                                 21

<210> SEQ ID NO 27
<211> LENGTH: 25
<212> TYPE: DNA
<213> ORGANISM: Artificial seqeunce
<220> FEATURE:
<223> OTHER INFORMATION: PSO333209 antisense primer, PSO333209JK-A

<400> SEQUENCE: 27
tgaccttaac acacccatca caagt                                             25

<210> SEQ ID NO 28
<211> LENGTH: 22
<212> TYPE: DNA
<213> ORGANISM: Artificial seqeunce
<220> FEATURE:
<223> OTHER INFORMATION: SAMS forward primer: (SAMS-48F)

<400> SEQUENCE: 28
ggaagaagag aatcgggtgg tt                                                22

<210> SEQ ID NO 29
<211> LENGTH: 23
<212> TYPE: DNA
<213> ORGANISM: Artificial seqeunce
<220> FEATURE:
<223> OTHER INFORMATION: FAM labeled SAMS probe: (SAMS-88T)

<400> SEQUENCE: 29
attgtgttgt gtggcatggt tat                                               23

<210> SEQ ID NO 30
<211> LENGTH: 23
<212> TYPE: DNA
<213> ORGANISM: Artificial seqeunce
<220> FEATURE:
<223> OTHER INFORMATION: SAMS reverse primer: (SAMS-134R)
```

-continued

<400> SEQUENCE: 30
ggcttgttgt gcagtttttg aag                                          23

<210> SEQ ID NO 31
<211> LENGTH: 20
<212> TYPE: DNA
<213> ORGANISM: Artificial seqeunce
<220> FEATURE:
<223> OTHER INFORMATION: YFP forward primer: (YFP-67F)

<400> SEQUENCE: 31
aacggccaca agttcgtgat                                              20

<210> SEQ ID NO 32
<211> LENGTH: 20
<212> TYPE: DNA
<213> ORGANISM: Artificial seqeunce
<220> FEATURE:
<223> OTHER INFORMATION: FAM labeled YFP probe: (YFP-88T)

<400> SEQUENCE: 32
accggcgagg gcatcggcta                                              20

<210> SEQ ID NO 33
<211> LENGTH: 20
<212> TYPE: DNA
<213> ORGANISM: Artificial seqeunce
<220> FEATURE:
<223> OTHER INFORMATION: YFP reverse primer: (YFP-130R)

<400> SEQUENCE: 33
cttcaagggc aagcagacca                                              20

<210> SEQ ID NO 34
<211> LENGTH: 24
<212> TYPE: DNA
<213> ORGANISM: Artificial seqeunce
<220> FEATURE:
<223> OTHER INFORMATION: HSP forward primer: (HSP-F1)

<400> SEQUENCE: 34
caaacttgac aaagccacaa ctct                                         24

<210> SEQ ID NO 35
<211> LENGTH: 20
<212> TYPE: DNA
<213> ORGANISM: Artificial seqeunce
<220> FEATURE:
<223> OTHER INFORMATION: VIC labeled HSP probe: (HSP probe)

<400> SEQUENCE: 35
ctctcatctc atataaatac                                              20

<210> SEQ ID NO 36
<211> LENGTH: 21
<212> TYPE: DNA
<213> ORGANISM: Artificial seqeunce
<220> FEATURE:
<223> OTHER INFORMATION: HSP reverse primer: (HSP-R1)

<400> SEQUENCE: 36
ggagaaattg gtgtcgtgga a                                            21

<210> SEQ ID NO 37
<211> LENGTH: 100
<212> TYPE: DNA

```
<213> ORGANISM: Artificial seqeunce
<220> FEATURE:
<223> OTHER INFORMATION: AttL1

<400> SEQUENCE: 37
caaataatga ttttattttg actgatagtg acctgttcgt tgcaacaaat tgataagcaa      60 tgcttttta taatgccaac tttgtacaaa aaagcaggct                            100

<210> SEQ ID NO 38
<211> LENGTH: 100
<212> TYPE: DNA
<213> ORGANISM: Artificial seqeunce
<220> FEATURE:
<223> OTHER INFORMATION: AttL2

<400> SEQUENCE: 38
caaataatga ttttattttg actgatagtg acctgttcgt tgcaacaaat tgataagcaa      60
tgctttctta taatgccaac tttgtacaag aaagctgggt                           100

<210> SEQ ID NO 39
<211> LENGTH: 125
<212> TYPE: DNA
<213> ORGANISM: Artificial seqeunce
<220> FEATURE:
<223> OTHER INFORMATION: AttR1

<400> SEQUENCE: 39
acaagtttgt acaaaaaagc tgaacgagaa acgtaaaatg atataaatat caatatatta      60
aattagattt tgcataaaaa acagactaca taatactgta aaacacaaca tatccagtca    120
ctatg                                                                125

<210> SEQ ID NO 40
<211> LENGTH: 125
<212> TYPE: DNA
<213> ORGANISM: Artificial seqeunce
<220> FEATURE:
<223> OTHER INFORMATION: AttR2

<400> SEQUENCE: 40
accactttgt acaagaaagc tgaacgagaa acgtaaaatg atataaatat caatatatta      60
aattagattt tgcataaaaa acagactaca taatactgta aaacacaaca tatccagtca    120
ctatg                                                                125

<210> SEQ ID NO 41
<211> LENGTH: 21
<212> TYPE: DNA
<213> ORGANISM: Artificial seqeunce
<220> FEATURE:
<223> OTHER INFORMATION: AttB1

<400> SEQUENCE: 41
caagtttgta caaaaaagca g                                               21

<210> SEQ ID NO 42
<211> LENGTH: 21
<212> TYPE: DNA
<213> ORGANISM: Artificial seqeunce
<220> FEATURE:
<223> OTHER INFORMATION: AttB2

<400> SEQUENCE: 42
cagctttctt gtacaaagtg g                                               21
```

<210> SEQ ID NO 43
<211> LENGTH: 8409
<212> TYPE: DNA
<213> ORGANISM: Artificial seqeunce
<220> FEATURE:
<223> OTHER INFORMATION: plasmid QC324i

<400> SEQUENCE: 43

```
atcaaccact ttgtacaaga aagctgaacg agaaacgtaa aatgatataa atatcaatat      60
attaaattag attttgcata aaaaacagac tacataatac tgtaaaacac aacatatcca     120
gtcactatgg tcgacctgca gactggctgt gtataaggga gcctgacatt tatattcccc     180
agaacatcag gttaatggcg tttttgatgt cattttcgcg gtggctgaga tcagccactt     240
cttcccgat aacggagacc ggcacactgg ccatatcggt ggtcatcatg cgccagcttt      300
catccccgat atgcaccacc gggtaaagtt cacgggagac tttatctgac agcagacgtg     360
cactggccag ggggatcacc atccgtcgcc cgggcgtgtc aataatatca ctctgtacat     420
ccacaaacag acgataacgg ctctctcttt tataggtgta aaccttaaac tgcatttcac     480
cagcccctgt tctcgtcagc aaaagagccg ttcatttcaa taaaccgggc gacctcagcc     540
atcccttcct gattttccgc tttccagcgt tcggcacgca gacgacgggc ttcattctgc     600
atggttgtgc ttaccagacc ggagatattg acatcatata tgccttgagc aactgatagc     660
tgtcgctgtc aactgtcact gtaatacgct gcttcatagc atacctcttt ttgacatact     720
tcgggtatac atatcagtat atattcttat accgcaaaaa tcagcgcgca atacgcata      780
ctgttatctg gcttttagta agccggatcc agatctttac gccccgccct gccactcatc     840
gcagtactgt tgtaattcat taagcattct gccgacatgg aagccatcac aaacggcatg     900
atgaacctga atcgccagcg gcatcagcac cttgtcgcct tgcgtataat atttgcccat     960
ggtgaaaacg ggggcgaaga agttgtccat attggccacg tttaaatcaa actggtgaa     1020
actcacccag ggattggctg agacgaaaaa catattctca ataaaccctt tagggaaata    1080
ggccaggttt tcaccgtaac acgccacatc ttgcgaatat atgtgtagaa actgccggaa    1140
atcgtcgtgg tattcactcc agagcgatga aaacgtttca gtttgctcat ggaaaacggt    1200
gtaacaaggg tgaacactat cccatatcac cagctcaccg tctttcattg ccatacggaa    1260
ttccggatga gcattcatca ggcgggcaag aatgtgaata aaggccggat aaaacttgtg    1320
cttatttttc tttacggtct ttaaaaaggc cgtaatatcc agctgaacgg tctggttata    1380
ggtacattga gcaactgact gaaatgcctc aaaatgttct ttacgatgcc attgggatat    1440
atcaacggtg gtatatccag tgatttttt ctccatttta gcttccttag ctcctgaaaa    1500
tctcgacgga tcctaactca aaatccacac attatacgag ccggaagcat aaagtgtaaa    1560
gcctggggtg cctaatgcgg ccgccaatat gactggatat gttgtgtttt acagtattat    1620
gtagtctgtt tttatgcaa atctaatttt aatatattga tatttatatc attttacgtt    1680
tctcgttcag cttttttgta caaacttgtt gatggggtta acatatcata acttcgtata    1740
atgtatgcta tacgaagtta taggcctgga tcttcgaggt cgagcggccg cagatttagg    1800
tgacactata gaatatgcat cactagtaag ctttgctcta gatcaaactc acatccaaac    1860
ataacatgga tatcttcctt accaatcata ctaattattt tgggttaaat attaatcatt    1920
attttaaga tattaattaa gaaattaaaa gatttttaa aaaaatgtat aaaattatat      1980
tattcatgat ttttcataca tttgattttg ataataaata tatttttttt aatttcttaa    2040
aaaatgttgc aagacactta ttagacatag tcttgttctg tttacaaaag cattcatcat    2100
```

```
ttaatacatt aaaaaatatt taatactaac agtagaatct tcttgtgagt ggtgtgggag    2160
taggcaacct ggcattgaaa cgagagaaag agagtcagaa ccagaagaca aataaaaagt    2220
atgcaacaaa caaatcaaaa tcaaagggca aaggctgggg ttggctcaat tggttgctac    2280
attcaatttt caactcagtc aacggttgag attcactctg acttccccaa tctaagccgc    2340
ggatgcaaac ggttgaatct aacccacaat ccaatctcgt tacttagggg cttttccgtc    2400
attaactcac ccctgccacc cggtttccct ataaattgga actcaatgct ccctctaaa    2460 ctcgtatcgc ttcagagttg agaccaagac acactcgttc atatatctct ctgctcttct    2520
cttctcttct acctctcaag gtacttttct tctccctcta ccaaatccta gattccgtgg    2580
ttcaatttcg gatcttgcac ttctggtttg ctttgccttg cttttttcctc aactgggtcc    2640 atctaggatc catgtgaaac tctactcttt ctttaatatc tgcggaatac gcgtttgact    2700
ttcagatcta gtcgaaatca tttcataatt gcctttcttt cttttagctt atgagaaata    2760
aaatcacttt ttttttattt caaaataaac cttgggcctt gtgctgactg agatggggtt    2820
tggtgattac agaattttag cgaattttgt aattgtactt gtttgtctgt agttttgttt    2880
tgttttcttg tttctcatac attccttagg cttcaatttt attcgagtat aggtcacaat    2940
aggaattcaa actttgagca ggggaattaa tcccttcctt caaatccagt tgtttgtat    3000 atatgtttaa aaaatgaaac ttttgcttta aattctatta taacttttttt tatggctgaa    3060 attttgcat gtgtctttgc tctctgttgt aaatttactg tttaggtact aactctaggc    3120
ttgttgtgca gtttttgaag tataaccatg ccacacaaca caatggcggc caccgcttcc    3180
agaaccaccc gattctcttc ttcctcttca cacccacct tccccaaacg cattactaga    3240
tccaccctcc ctctctctca tcaaaccctc accaaaccca accacgctct caaaatcaaa    3300
tgttccatct ccaaaccccc cacggcggcg cccttcacca aggaagcgcc gaccacggag    3360
cccttcgtgt cacggttcgc ctccggcgaa cctcgcaagg gcgcggacat ccttgtggag    3420
gcgctggaga ggcagggcgt gacgacggtg ttcgcgtacc ccggcggtgc gtcgatggag    3480
atccaccagg cgctcacgcg ctccgccgcc atccgcaacg tgctcccgcg ccacgagcag    3540
ggcggcgtct tcgccgccga aggctacgcg cgttcctccg cctccccgg cgtctgcatt    3600 gccacctccg gccccggcgc caccaacctc gtgagcggcc tcgccgacgc tttaatggac    3660
agcgtcccag tcgtcgccat caccggccag gtcgcccgcc ggatgatcgg caccgacgcc    3720
ttccaagaaa ccccgatcgt ggaggtgagc agatccatca cgaagcacaa ctacctcatc    3780
ctcgacgtcg acgacatccc ccgcgtcgtc gccgaggctt tcttcgtcgc cacctccggc    3840
cgccccggtc cggtcctcat cgacattccc aaagacgttc agcagcaact cgccgtgcct    3900
aattgggacg agcccgttaa cctccccggt tacctcgcca ggctgcccag gcccccgcc    3960 gaggcccaat tggaacacat tgtcagactc atcatggagg cccaaaagcc cgttctctac    4020
gtcggcggtg gcagtttgaa ttccagtgct gaattgaggc gctttgttga actcactggt    4080
attcccgttg ctagcacttt aatgggtctt ggaacttttc ctattggtga tgaatattcc    4140
cttcagatgc tgggtatgca tggtactgtt tatgctaact atgctgttga caatagtgat    4200
ttgttgcttg cctttgggt aaggtttgat gaccgtgtta ctgggaagct tgaggctttt    4260
gctagtaggg ctaagattgt tcacattgat attgattctg ccgagattgg gaagaacaag    4320
caggcgcacg tgtcggtttg cgcggatttg aagttggcct tgaagggaat taatatgatt    4380
ttggaggaga aaggagtgga gggtaagttt gatcttggag gttggagaga agagattaat    4440
gtgcagaaac acaagtttcc attgggttac aagacattcc aggacgcgat ttctccgcag    4500
```

```
catgctatcg aggttcttga tgagttgact aatggagatg ctattgttag tactggggtt    4560
gggcagcatc aaatgtgggc tgcgcagttt tacaagtaca agagaccgag gcagtggttg    4620
acctcagggg gtcttggagc catgggtttt ggattgcctg cggctattgg tgctgctgtt    4680
gctaaccctg gggctgttgt ggttgacatt gatggggatg gtagtttcat catgaatgtt    4740
caggagttgg ccactataag agtggagaat ctcccagtta agatattgtt gttgaacaat    4800
cagcatttgg gtatggtggt tcagttggag gataggttct acaagtccaa tagagctcac    4860
acctatcttg gagatccgtc tagcgagagc gagatattcc caaacatgct caagtttgct    4920
gatgcttgtg ggataccggc agcgcgagtg acgaagaagg aagagcttag agcggcaatt    4980
cagagaatgt tggacacccc tggcccctac cttcttgatg tcattgtgcc ccatcaggag    5040
catgtgttgc cgatgattcc cagtaatgga tccttcaagg atgtgataac tgagggtgat    5100
ggtagaacga ggtactgatt gcctagacca aatgttcctt gatgcttgtt ttgtacaata    5160
tatataagat aatgctgtcc tagttgcagg atttggcctg tggtgagcat catagtctgt    5220
agtagttttg gtagcaagac atttttatttt cctttttattt aacttactac atgcagtagc    5280
atctatctat ctctgtagtc tgatatctcc tgttgtctgt attgtgccgt tggattttt     5340
gctgtagtga gactgaaaat gatgtgctag taataatatt tctgttagaa atctaagtag    5400
agaatctgtt gaagaagtca aaagctaatg gaatcaggtt acatattcaa tgtttttctt    5460
tttttagcgg ttggtagacg tgtagattca acttctcttg gagctcacct aggcaatcag    5520
taaaatgcat attccttttt taacttgcca tttatttact tttagtggaa attgtgacca    5580
atttgttcat gtagaacgga tttggaccat tgcgtccaca aaacgtctct tttgctcgat    5640
cttcacaaag cgataccgaa atccagagat agttttcaaa agtcagaaat ggcaaagtta    5700
taaatagtaa aacagaatag atgctgtaat cgacttcaat aacaagtggc atcacgtttc    5760
tagttctaga cccatcagat cgaattaaca tatcataact tcgtataatg tatgctatac    5820
gaagttatag gcctggatcc actagttcta gagcggccgc tcgagggggg gcccggtacc    5880
ggcgcgccgt tctatagtgt cacctaaatc gtatgtgtat gatacataag gttatgtatt    5940
aattgtagcc gcgttctaac gacaatatgt ccatatggtg cactctcagt acaatctgct    6000
ctgatgccgc atagttaagc cagccccgac acccgccaac acccgctgac gcgccctgac    6060
gggcttgtct gctcccggca tccgcttaca gacaagctgt gaccgtctcc gggagctgca    6120
tgtgtcagag gttttcaccg tcatcaccga aacgcgcgag acgaaagggc ctcgtgatac    6180
gcctattttt ataggttaat gtcatgacca aaatccctta acgtgagttt tcgttccact    6240
gagcgtcaga ccccgtagaa aagatcaaag gatcttcttg agatcctttt tttctgcgcg    6300
taatctgctg cttgcaaaca aaaaaaccac cgctaccagc ggtggtttgt ttgccggatc    6360
aagagctacc aactcttttt ccgaaggtaa ctggcttcag cagagcgcag ataccaaata    6420
ctgtcctttct agtgtagccg tagttaggcc accacttcaa gaactctgta gcaccgccta    6480
catacctcgc tctgctaatc ctgttaccag tggctgctgc cagtggcgat aagtcgtgtc    6540
ttaccgggtt ggactcaaga cgatagttac cggataaggc gcagcggtcg ggctgaacgg    6600
ggggttcgtg cacacagccc agcttggagc gaacgaccta caccgaactg agatacctac    6660
agcgtgagca ttgagaaagc gccacgcttc ccgaagggag aaaggcggac aggtatccgg    6720
taagcggcag ggtcggaaca ggagagcgca cgagggagct tccaggggga aacgcctggt    6780
atctttatag tcctgtcggg tttcgccacc tctgacttga gcgtcgattt ttgtgatgct    6840
cgtcaggggg gcggagccta tggaaaaacg ccagcaacgc ggcctttta cggttcctgg    6900
```

```
ccttttgctg gccttttgct cacatgttct ttcctgcgtt atccctgat tctgtggata    6960
accgtattac cgcctttgag tgagctgata ccgctcgccg cagccgaacg accgagcgca    7020
gcgagtcagt gagcgaggaa gcggaagagc gcccaatacg caaaccgcct ctccccgcgc    7080
gttggccgat tcattaatgc aggttgatca gatctcgatc ccgcgaaatt aatacgactc    7140
actatagggA gaccacaacg gtttccctct agaaataatt ttgtttaact ttaagaagga    7200
gatataccca tggaaaagcc tgaactcacc gcgacgtctg tcgagaagtt tctgatcgaa    7260
aagttcgaca gcgtctccga cctgatgcag ctctcggagg gcgaagaatc tcgtgctttc    7320
agcttcgatg taggagggcg tggatatgtc ctgcgggtaa atagctgcgc cgatggtttc    7380
tacaaagatc gttatgttta tcggcacttt gcatcggccg cgctcccgat tccggaagtg    7440
cttgacattg gggaattcag cgagagcctg acctattgca tctcccgccg tgcacagggt    7500
gtcacgttgc aagacctgcc tgaaaccgaa ctgcccgctg ttctgcagcc ggtcgcggag    7560
gctatggatg cgatcgctgc ggccgatctt agccagacga gcgggttcgg cccattcgga    7620
ccgcaaggaa tcggtcaata cactacatgg cgtgatttca tatgcgcgat tgctgatccc    7680
catgtgtatc actggcaaac tgtgatggac gacaccgtca gtgcgtccgt cgcgcaggct    7740
ctcgatgagc tgatgctttg gccgaggac tgccccgaag tccggcacct cgtgcacgcg    7800
gatttcggct ccaacaatgt cctgacggac aatggccgca taacagcggt cattgactgg    7860
agcgaggcga tgttcgggga ttcccaatac gaggtcgcca acatcttctt ctggaggccg    7920
tggttggctt gtatggagca gcagacgcgc tacttcgagc ggaggcatcc ggagcttgca    7980
ggatcgccgc ggctccgggc gtatatgctc cgcattggtc ttgaccaact ctatcagagc    8040
ttggttgacg gcaatttcga tgatgcagct tgggcgcagg tcgatgcga cgcaatcgtc    8100
cgatccggag ccgggactgt cgggcgtaca caaatcgccc gcagaagcgc ggccgtctgg    8160
accgatggct gtgtagaagt actcgccgat agtggaaacc gacgcccag cactcgtccg    8220
agggcaaagg aatagtgagg tacagcttgg atcgatccgg ctgctaacaa agcccgaaag    8280
gaagctgagt tggctgctgc caccgctgag caataactag cataaccct tggggcctct    8340
aaacgggtct gagggggttt tttgctgaaa ggaggaacta tatccggatg atcgggcgcg    8400
ccggtaccc                                                             8409
```

<210> SEQ ID NO 44
<211> LENGTH: 5286
<212> TYPE: DNA
<213> ORGANISM: Artificial seqeunce
<220> FEATURE:
<223> OTHER INFORMATION: plasmid QC330

<400> SEQUENCE: 44

```
atcaacaagt ttgtacaaaa aagctgaacg agaaacgtaa aatgatataa atatcaatat     60
attaaattag attttgcata aaaaacagac tacataatac tgtaaaacac aacatatcca    120
gtcatattgg cggccgcatt aggcaccca ggctttacac tttatgcttc cggctcgtat    180
aatgtgtgga ttttgagtta ggatccgtcg agattttcag gagctaagga agctaaaatg    240
gagaaaaaaa tcactggata taccaccgtt gatatatccc aatggcatcg taaagaacat    300
tttgaggcat ttcagtcagt tgctcaatgt acctataacc agaccgttca gctggatatt    360
acggccttt taaagaccgt aaagaaaaat aagcacaagt tttatccggc ctttattcac    420
attcttgccc gcctgatgaa tgctcatccg gaattccgta tggcaatgaa agacggtgag    480
ctggtgatat gggatagtgt tcaccccttgt tacaccgttt ccatgagca aactgaaacg    540
```

```
ttttcatcgc tctggagtga ataccacgac gatttccggc agtttctaca catatattcg    600
caagatgtgg cgtgttacgg tgaaaacctg gcctatttcc ctaaagggtt tattgagaat    660 atgttttcg tctcagccaa tccctgggtg agtttcacca gttttgattt aaacgtggcc    720
aatatggaca acttcttcgc ccccgttttc accatgggca aatattatac gcaaggcgac    780
aaggtgctga tgccgctggc gattcaggtt catcatgccg tttgtgatgg cttccatgtc    840
ggcagaatgc ttaatgaatt acaacagtac tgcgatgagt ggcagggcgg ggcgtaaaga    900
tctggatccg gcttactaaa agccagataa cagtatgcgt atttgcgcgc tgattttgc     960 ggtataagaa tatatactga tatgtatacc cgaagtatgt caaaaagagg tatgctatga   1020
agcagcgtat tacagtgaca gttgacagcg acagctatca gttgctcaag gcatatatga   1080
tgtcaatatc tccggtctgg taagcacaac catgcagaat gaagcccgtc gtctgcgtgc   1140
cgaacgctgg aaagcggaaa tcaggaagg atggctgag gtcgcccggt ttattgaaat    1200
gaacggctct tttgctgacg agaacagggg ctggtgaaat gcagtttaag gtttacacct   1260
ataaaagaga gagccgttat cgtctgtttg tggatgtaca gagtgatatt attgacacgc   1320
ccgggcgacg gatggtgatc cccctggcca gtgcacgtct gctgtcagat aaagtctccc   1380
gtgaacttta cccggtggtg catatcgggg atgaaagctg gcgcatgatg accaccgata   1440
tggccagtgt gccggtctcc gttatcgggg aagaagtggc tgatctcagc caccgcgaaa   1500
atgacatcaa aaacgccatt aacctgatgt tctggggaat ataaatgtca ggctccctta   1560
tacacagcca gtctgcaggt cgaccatagt gactggatat gttgtgtttt acagtattat   1620
gtagtctgtt ttttatgcaa aatctaattt aatatattga tattatatc attttacgtt    1680 tctcgttcag cttcttgta caaagtggtt gatgggatcc atgggccaca gcaagcacgg   1740
cctgaaggag gagatgacca tgaagtacca catggagggc tgcgtgaacg gccacaagtt   1800
cgtgatcacc ggcagggca tcggctaccc cttcaagggc aagcagacca tcaacctgtg   1860
cgtgatcgag ggcggccccc tgcccttcag cgaggacatc ctgagcgccg gcttcaagta   1920
cggcgaccgg atcttcaccg agtaccccca ggacatcgtg gactacttca agaacagctg   1980
ccccgccggc tacacctggg gccggagctt cctgttcgag gacggcgccg tgtgcatctg   2040
taacgtggac atcaccgtga gcgtgaagga gaactgcatc taccacaaga gcatcttcaa   2100
cggcgtgaac ttccccgccg acggcccgt gatgaagaag atgaccacca actgggaggc   2160
cagctgcgag aagatcatgc ccgtgcctaa gcagggcatc ctgaagggcg acgtgagcat   2220
gtacctgctg ctgaaggacg gcggccgta ccggtgccag ttcgacaccg tgtacaaggc   2280
caagagcgtg cccagcaaga tgcccgagtg cacttcatc cagcacaagc tgctgcggga   2340
ggaccggagc gacgccaaga accagaagtg gcagctgacc gagcacgcca tcgccttccc   2400
cagcgccctg gcctgagagc tcgaatttcc ccgatcgttc aaacatttgg caataaagtt   2460
tcttaagatt gaatcctgtt gccggtcttg cgatgattat catataattt ctgttgaatt   2520
acgttaagca tgtaataatt aacatgtaat gcatgacgtt atttatgaga tgggttttta   2580
tgattagagt cccgcaatta tacatttaat acgcgataga aaacaaaata tagcgcgcaa   2640
actaggataa attatcgcgc gcggtgtcat ctatgttact agatcgggaa ttctagtggc   2700
cggcccagct gatatccatc acactggcgg ccgctcgagt ctatagtgt cacctaaatc    2760 gtatgtgtat gatacataag gttatgtatt aattgtagcc gcgttctaac gacaatatgt   2820
ccatatggtg cactctcagt acaatctgct ctgatgccgc atagttaagc cagcccgac    2880 acccgccaac acccgctgac gcgccctgac gggcttgtct gctcccggca tccgcttaca   2940
```

```
gacaagctgt gaccgtctcc gggagctgca tgtgtcagag gttttcaccg tcatcaccga    3000
aacgcgcgag acgaagggc ctcgtgatac gcctattttt ataggttaat gtcatgacca    3060 aaatcccctta acgtgagttt tcgttccact gagcgtcaga ccccgtagaa aagatcaaag   3120
gatcttcttg agatccttt tttctgcgcg taatctgctg cttgcaaaca aaaaaaccac    3180
cgctaccagc ggtggtttgt ttgccggatc aagagctacc aactctttt ccgaaggtaa    3240 ctggcttcag cagagcgcag ataccaaata ctgtccttct agtgtagccg tagttaggcc    3300
accacttcaa gaactctgta gcaccgccta catacctcgc tctgctaatc ctgttaccag    3360
tggctgctgc cagtggcgat aagtcgtgtc ttaccgggtt ggactcaaga cgatagttac    3420
cggataaggc gcagcggtcg ggctgaacgg ggggttcgtg cacacagccc agcttggagc    3480
gaacgaccta caccgaactg agatacctac agcgtgagca ttgagaaagc gccacgcttc    3540
ccgaagggag aaaggcggac aggtatccgg taagcggcag ggtcggaaca ggagagcgca    3600
cgagggagct ccaggggga aacgcctggt atctttatag tcctgtcggg tttcgccacc    3660
tctgacttga gcgtcgattt tgtgatgct cgtcaggggg gcggagccta tggaaaaacg    3720
ccagcaacgc ggccttttta cggttcctgg ccttttgctg ccttttgct cacatgttct    3780 ttcctgcgtt atcccctgat tctgtggata accgtattac cgccttttgag tgagctgata    3840 ccgctcgccg cagccgaacg accgagcgca gcgagtcagt gagcgaggaa gcggaagagc    3900
gcccaatacg caaaccgcct ctccccgcgc gttggccgat tcattaatgc aggttgatca    3960
gatctcgatc ccgcgaaatt aatacgactc actatagga gaccacaacg gtttccctct    4020
agaaataatt ttgtttaact ttaagaagga gatataccca tggaaaagcc tgaactcacc    4080
gcgacgtctg tcgagaagtt tctgatcgaa aagttcgaca gcgtctccga cctgatgcag    4140
ctctcggagg gcgaagaatc tcgtgctttc agcttcgatg taggagggcg tggatatgtc    4200
ctgcgggtaa atagctgcgc cgatggtttc tacaaagatc gttatgttta tcggcacttt    4260
gcatcggccg cgctcccgat tccggaagtg cttgacattg ggaattcag cgagagcctg    4320 acctattgca tctcccgccg tgcacagggt gtcacgttgc aagacctgcc tgaaaccgaa    4380
ctgcccgctg ttctgcagcc ggtcgcgag gctatgatg cgatcgctgc ggccgatctt    4440
agccagacga gcgggttcgg cccattcgga ccgcaaggaa tcggtcaata cactacatgg    4500
cgtgatttca tatgcgcgat tgctgatccc catgtgtatc actggcaaac tgtgatggac    4560
gacaccgtca gtgcgtccgt cgcgcaggct ctcgatgagc tgatgctttg gccgaggac    4620 tgccccgaag tccggcacct cgtgcacgcg gatttcggct ccaacaatgt cctgacggac    4680
aatggccgca taacagcggt cattgactgg agcgaggcga tgttcgggga ttcccaatac    4740
gaggtcgcca acatcttctt ctggaggccg tggttggctt gtatgagca gcagacgcgc    4800 tacttcgagc ggaggcatcc ggagcttgca ggatcgccgc ggctccgggc gtatatgctc    4860
cgcattggtc ttgaccaact ctatcagagc ttggttgacg gcaatttcga tgatgcagct    4920
tgggcgcagg gtcgatgcga cgcaatcgtc cgatccggag ccgggactgt cgggcgtaca    4980
caaatcgccc gcagaagcgc ggccgtctgg accgatggct gtgtagaagt actcgccgat    5040
agtggaaacc gacgccccag cactcgtccg agggcaaagg aatagtgagg tacagcttgg    5100
atcgatccgg ctgctaacaa agcccgaaag gaagctgagt tggctgctgc caccgctgag    5160
caataactag cataaccccct tggggcctct aaacgggtct tgaggggttt tttgctgaaa    5220
ggaggaacta tatccggatg atcgtcgagg cctcacgtgt taacaagctt gcatgcctgc    5280
aggttt                                                               5286
```

```
<210> SEQ ID NO 45
<211> LENGTH: 564
<212> TYPE: DNA
<213> ORGANISM: Glycine max

<400> SEQUENCE: 45
cgcgggggtt ctagtgtgtg attgtttgtt gttgtaactc gttcttcttc ttttgttgtt      60
ctgtgattgt gtttgttttt tctctcacct gaaaatgtct tgctgcggtg gtaactgtgg     120
ttgcggaagc tcctgcaagt gcggcaacgg ctgcggaggc tgcaagatgt acccagactt     180
gagctacact gagtcaacca ccaccgagac cttggtcatg ggagtggcac cagttaaggc     240
tcaattcgag agtgctgaaa tgggtgttcc cgctgagaac gatggctgca aatgtggagc     300
taactgcacc tgcaacccct gcacttgcaa gtgaggtgtt ggagagctaa agcttcaagc     360
agaaatggcc cttagaaata atgataaaaa ctatatgtag tttcaaaact tcaaaattat     420
gtagtatgta ttatgttgca ctctggtgtt ttgtgtctaa acaaacaccc ttagaataaa     480
gtggtcattt cttgcccttg agcaagttca agtgttttgg acttgtgatg ggtgtgttga     540
aaaaaaaaaa aaaaaaaaaa aaaa                                             564

<210> SEQ ID NO 46
<211> LENGTH: 79
<212> TYPE: PRT
<213> ORGANISM: Glycine max

<400> SEQUENCE: 46

Met Ser Cys Cys Gly Gly Asn Cys Gly Cys Gly Ser Ser Cys Lys Cys
1               5                   10                  15

Gly Asn Gly Cys Gly Gly Cys Lys Met Tyr Pro Asp Leu Ser Tyr Thr
            20                  25                  30

Glu Ser Thr Thr Thr Glu Thr Leu Val Met Gly Val Ala Pro Val Lys
        35                  40                  45

Ala Gln Phe Glu Ser Ala Glu Met Gly Val Pro Ala Glu Asn Asp Gly
    50                  55                  60

Cys Lys Cys Gly Ala Asn Cys Thr Cys Asn Pro Cys Thr Cys Lys
65                  70                  75
```